(12) United States Patent
Del Gaudio et al.

(10) Patent No.: US 11,541,011 B2
(45) Date of Patent: Jan. 3, 2023

(54) IN SITU GELIFYING POWDER

(71) Applicant: MATERIAS S.r.l., Naples (IT)

(72) Inventors: Pasquale Del Gaudio, Angri (IT); Rita Patrizia Aquino, Avellino (IT); Paola Russo, Baronissi (IT); Gianluigi De Falco, Avellino (IT); Luigi Nicolais, Ercolano (IT)

(73) Assignee: MATERIAS S.r.l., Naples (IT)

( * ) Notice: Subject to any disclaimer, the term of this patent is extended or adjusted under 35 U.S.C. 154(b) by 0 days.

(21) Appl. No.: 16/761,837

(22) PCT Filed: Nov. 7, 2018

(86) PCT No.: PCT/IB2018/058742
§ 371 (c)(1),
(2) Date: May 6, 2020

(87) PCT Pub. No.: WO2019/092608
PCT Pub. Date: May 16, 2019

(65) Prior Publication Data
US 2021/0196634 A1    Jul. 1, 2021

(30) Foreign Application Priority Data

Nov. 8, 2017  (IT) .................. 102017000127474

(51) Int. Cl.
*A61K 9/08*        (2006.01)
*A61K 45/06*       (2006.01)
(Continued)

(52) U.S. Cl.
CPC .............. *A61K 9/1652* (2013.01); *A23B 4/20* (2013.01); *A23B 4/22* (2013.01); *A23B 4/24* (2013.01);
(Continued)

(58) Field of Classification Search
CPC .. A61K 2300/00; A61K 31/65; A61K 31/722; A61K 31/732; A61K 31/734;
(Continued)

(56) References Cited

U.S. PATENT DOCUMENTS 4,873,092 A * 10/1989 Azuma .................. A61K 9/205
                                                          424/499
5,482,932 A *  1/1996 Thompson .......... A61L 26/0023
                                                          514/54
(Continued)

FOREIGN PATENT DOCUMENTS

CN         104610579 A      5/2015
CN         104610757 A      5/2015
(Continued)

OTHER PUBLICATIONS

Archana et al. (Indian Journal of Biotechnology 2013;12:475-482) (Year: 2013).*

(Continued)

*Primary Examiner* — Ernst V Arnold
(74) *Attorney, Agent, or Firm* — Silvia Salvadori, P.C.; Silvia Salvadori

(57) ABSTRACT

A composition in powder form comprising alginic acid or sodium alginate, -pectin and chitosan, wherein the % by weight of the polysaccharides is at least 20% with respect to the total weight of the powder, the process for preparing the powder and its use in the treatment of cutaneous wounds and in the sector of food preservation are described.

10 Claims, 13 Drawing Sheets

(51) Int. Cl.
*A61K 47/36* (2006.01)
*A61K 9/16* (2006.01)
*A23B 4/20* (2006.01)
*A23B 4/22* (2006.01)
*A23B 4/24* (2006.01)
*A23L 3/3463* (2006.01)
*A23L 3/3544* (2006.01)
*A23L 3/358* (2006.01)
*A61K 9/14* (2006.01)

(52) U.S. Cl.
CPC .......... *A23L 3/34635* (2013.01); *A23L 3/358* (2013.01); *A23L 3/3544* (2013.01); *A61K 9/08* (2013.01); *A61K 9/146* (2013.01); *A61K 9/1682* (2013.01); *A61K 45/06* (2013.01); *A61K 47/36* (2013.01); *A23V 2002/00* (2013.01)

(58) Field of Classification Search
CPC .......... A61K 45/06; A61K 47/36; A61K 9/08; A61K 9/146; A61K 9/1652; A61K 9/1682; C08L 5/04; C08L 5/06; C08L 5/08; A23V 2002/00; A23V 2200/318; A23V 2250/5026; A23V 2250/5072; A23V 2250/511; A61P 17/02
See application file for complete search history.

(56) References Cited

U.S. PATENT DOCUMENTS

| | | | | |
|---|---|---|---|---|
| 5,836,970 | A | * | 11/1998 | Pandit .................. A61L 15/225 606/213 |
| 2001/0051613 | A1 | | 12/2001 | Illum et al. |
| 2015/0125538 | A1 | | 5/2015 | Li et al. |

FOREIGN PATENT DOCUMENTS

| | | | |
|---|---|---|---|
| CN | 104877180 | A | 9/2015 |
| CN | 104877353 | A | 9/2015 |
| CN | 104893003 | A | 9/2015 |
| EA | 016715 | B1 | 7/2012 |
| EP | 3115068 | A1 | 1/2017 |
| RU | 2005494 | C1 | 1/1994 |
| RU | 2519723 | C1 | 6/2014 |
| WO | 1998048814 | A1 | 11/1998 |
| WO | 2005023176 | A2 | 3/2005 |
| WO | 2007047994 | A2 | 4/2007 |
| WO | 2008103891 | A2 | 8/2008 |
| WO | 2010124387 | A1 | 11/2010 |

OTHER PUBLICATIONS

Hagesaether et al. (Pharmaceutical Development and Technology 2008;13:105-114) (Year: 2008).*
Yu et al. (Colloids and Surfaces B: Biointerfaces 2009;68:245-249). (Year: 2009).*
Karimi et al. (J Nanopharm Drug Deliv. 2013;1(3):266-278). (Year: 2013).*
Liu (Traditional Herbal Medicine Research Methods: Identification, Analysis, Bioassays, and Pharmaceutical and Clinical Studies 2011;John Wiley & Sons; section 6.3.1.; 1 page). (Year: 2011).*
Search Report and Written Opinion of PCT/IB2018/058742 dated Mar. 29, 2019.
Harun N. et al., "Optimization of process parameters for spray drying of tongkat ali extract", Journal of Engineering Science and Technology, special issue 6 Jan. 2015, pp. 31-34.
Office Action cited in corresponding Application No. 2020114324/04(023934) by the Russian Federation Patent Office dated Mar. 14, 2022.
Search Report issued by Russian Federation Patent Office dated Mar. 10, 2022 for Application No. 2020114324/04 (023934).
De Cicco F. et al., "Nanospray technology for an in situ gelling nanoparticulate powder as a wound dressing", International Journal of Pharmaceutics 473 (2014) 30-37.
Office Action dated Sep. 28, 2021 in connection with counterpart Chinese application No. 201880071939.3.
Translation No. 1 of relevant part of Office Action dated Sep. 28, 2021 in connection of counterpart Chinese application No. 201880071939.3.
Translation No. 2 of relevant part of Office Action dated Sep. 28, 2021 in connection of counterpart Chinese application No. 201880071939.3.
Translation No. 3 of relevant part of Office Action dated Sep. 28, 2021 in connection of counterpart Chinese application No. 201880071939.3.
Translation No. 4 of relevant part of Office Action dated Sep. 28, 2021 in connection of counterpart Chinese application No. 201880071939.3.

* cited by examiner

*p< 0.05, **p< 0.01 p<0.01, *p<0.005

IN SITU GELIFYING POWDER

This application is a U.S. national stage of PCT/IB2018/058742 filed on 7 Nov. 2018, which claims priority to and the benefit of Italian Application No. 102017000127474 filed on 8 Nov. 2017, the contents of which are incorporated herein by reference in their entireties.

The object of the present invention is a composition in the form of in situ gelifying powder; the process for preparing said powder and its use in the treatment of cutaneous wounds and in the field of food preservation are additional objects of the invention. Moreover, additional objects of the invention are the composition in the form of solution or liquid suspension that represents the starting material to obtain said powder and the process for preparing such liquid composition.

BACKGROUND OF THE INVENTION

Treatment of wounds is currently a problem throughout the world. The market of the products for the treatment of wounds is ample especially in developed countries like the USA, Europe and Japan that together account for more than 80% of global sales, but the market is also expected to grow in the developing Countries as a result of the expansion of health care services. Epidemiological data referred to 2014 show that approximately 2% of the adult population in Western Countries is affected by chronic wounds, and the percentage rises to 4% in the hospitalized population. The treatment of wounds is a challenge because it is a complex and sequential process. Acute wounds can evolve towards chronic wounds or can be infected by bacteria; in both cases these events stop the healing phase of the wound. For these reasons there is a certain pressure by the medical system to develop new therapies, that have an advantageous cost/benefit ratio with regard to both medical costs and social costs.

Products for the treatment of wounds are essentially intended for the healing of the wound and controlling the infection. Several products are currently available on the market, for example: traditional products such as adhesive bandages, topical ointments, gauze and sutures; innovative products such as medications based on alginate and hydrocolloids; active products such as skin substitutes, cell-based substitutes, collagen-based medications, growth factors; debriding products such as detergents and sealants; antimicrobial medications, for example based on silver or other antimicrobial agents; specialised medications for the treatment of diabetic foot ulcer (DFU), pressure ulcers (PU) and venous leg ulcers (VLU).

The treatment of chronic wounds is particularly challenging because currently available products have several adverse/collateral effects, for example local irritation and contact sensitization, immune reactions, absorption of the product, dehydration of the medication and/or the site of the wound, removal trauma at the time the medication is changed, need to change the medication frequently, with consequent effect on treatment costs.

Currently available are some innovative products based on hydrophilic polymers, above all alginate, pectin, hyaluronic acid and derivatives thereof; these products can be in the form of bandages, non-woven gauze, transparent films, ointments, sprays and granules that in contact with a wound give rise to the formation of a colloidal gel. Such products have a good capacity of retaining and absorbing the exudate formed by the wound, which reduce the risk of exudate leakage, skin maceration and the need for frequent changes of the medication.

For example, microparticles consisting of gentamicin/alginate/pectin are described in Aquino R P et al, (2013) International Journal of Pharmaceutics 440: 188-194; these microparticles were prepared by supercritical assisted atomization (SAA) and they are useful for the treatment of the bacterial infections of wounds.

The in situ formation of a hydrogel starting from microparticles consisting of gentamicin/alginate/pectin is described in De Cicco F et al, (2014), Carbohydrate Polymers 101:1216-1224; in this study, the microparticles were prepared by SAA technology or by spray drying.

The use of the nanospray drying technology in the preparation of an inhalation powder containing ketoprofen lysinate is described for example in Aquino R P et al, (2014), The Scientific World Journal ID 838410, 7 pages.

A nanoparticle powder consisting of gentamicin/alginate/pectin is described in De Cicco et al, (2014), International Journal of Pharmaceutics 473: 30-37; such powder, able to gelify in situ, was prepared by nanospray drying technology. In spite of recent developments, there is still a strong need in the health care field in relation to the treatment of wounds.

SUMMARY OF THE INVENTION

The present inventors have confronted the problem of treating wounds, especially in the case of chronic and/or ulcerous wounds.

In particular, the present inventors addressed the problem of reducing gelification times when the powder is placed in contact with the wound and of improving the capacity of a powder to absorb the exudate of the wounds.

Moreover, the present inventors addressed the problem of improving the adhesive capacity of the gel formed in situ, to avoid the risk of accidental detachment while allowing an easy removal of the gel from the wound after use.

The present inventors also addressed the problem of causing the gel formed in situ to have an adequate water vapour transmission rate to maintain a balanced hydration of the wound, preventing the exudate from determining excessive hydration of the wound or the gel formed as a result of the absorption of the exudate from causing occlusive phenomena.

The present inventors have found a specific composition in the form of in situ gelifying powder that is able to improve the treatment of wounds, especially of chronic and/or ulcerous wounds.

As will be discussed in greater depth in the experimental part, the composition of the invention has shorter gelification times than the gelification times of the alginate/pectin composition described by De Cicco et al, (2014), International Journal of Pharmaceutics 473: 30-37 and a high capacity of absorbing the exudate (see example 5).

Moreover, the gel formed in situ when the composition of the invention is placed in contact with a wound has an improved adhesive capacity with respect to the adhesive capacity of the gel described in De Cicco et al, (2014), International Journal of Pharmaceutics 473: 30-37 (see example 6); the gel formed by the powder of the invention also has a water vapour transmission rate that is adequate to maintain a balanced hydration of the wound (see example 7). Lastly, the specific composition of the invention induces cell migration in a statistically significant manner with respect to the alginate/pectin composition (example 8).

In addition, the in situ gelifying powder of the invention has an interesting field of application also in the sector of food preservation. Indeed, fresh food, for example meats, fruit, vegetables, etc., release fluids that increase the possibility of microbial pollution and reduce the shelf-life of foods, as pointed out in Biji et al; (2015), Journal of Food Science and Technology 52: 6125-6135. The in situ gelifying powder according to the invention is able to control microbial development even without the addition of active ingredients having antimicrobial activities (see example 10), therefore its use allows a prolongation of the quality, safety and sensorial properties of the food to be preserved, serving as active packaging for fresh food products.

Therefore, a first object of the invention is a composition in powder form comprising the following polysaccharides
alginic acid or sodium alginate,
pectin,
chitosan,
wherein the % by weight of the polysaccharides is at least 20% with respect to the total weight of the powder.

A second object of the invention is a composition in liquid solution or suspension form comprising the following polysaccharides
alginic acid or sodium alginate,
pectin,
chitosan.

A third object of the invention is the composition in powder form as defined in the first object of the invention, for use as a medicament.

A fourth object of the invention is the composition in powder form as defined in the first object of the invention, for use in the treatment of cutaneous wounds.

A fifth object of the invention is a method for treating a cutaneous wound in a patient by the application to said wound of a composition in powder form as defined in the first object of the invention, in an effective quantity for treating said wound.

A sixth object of the invention is the use of the composition in powder form as defined in the first object of the invention, for application to cutaneous wounds.

A seventh object of the invention is the process for preparing the composition in powder form as defined in the first object of the invention by an atomization process.

An eighth object of the invention is the process for preparing the composition in liquid solution, or suspension, form as defined in the second object of the invention.

A ninth object of the invention is the use of the composition in powder form as defined in the first object of the invention, in the field of food.

FIGURES

Figure 2A:
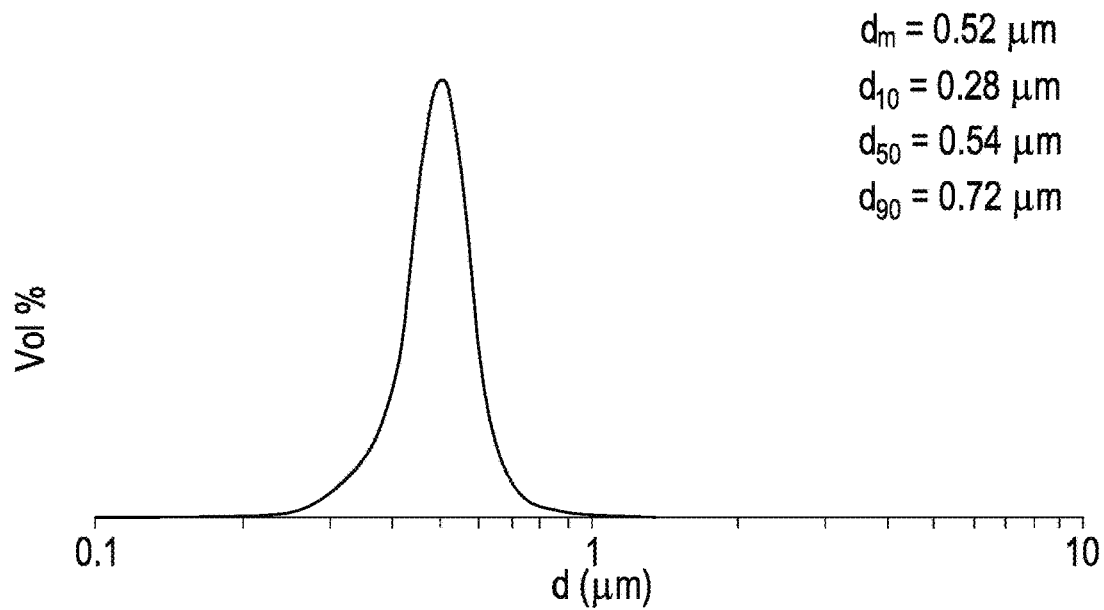
Figure 2A:
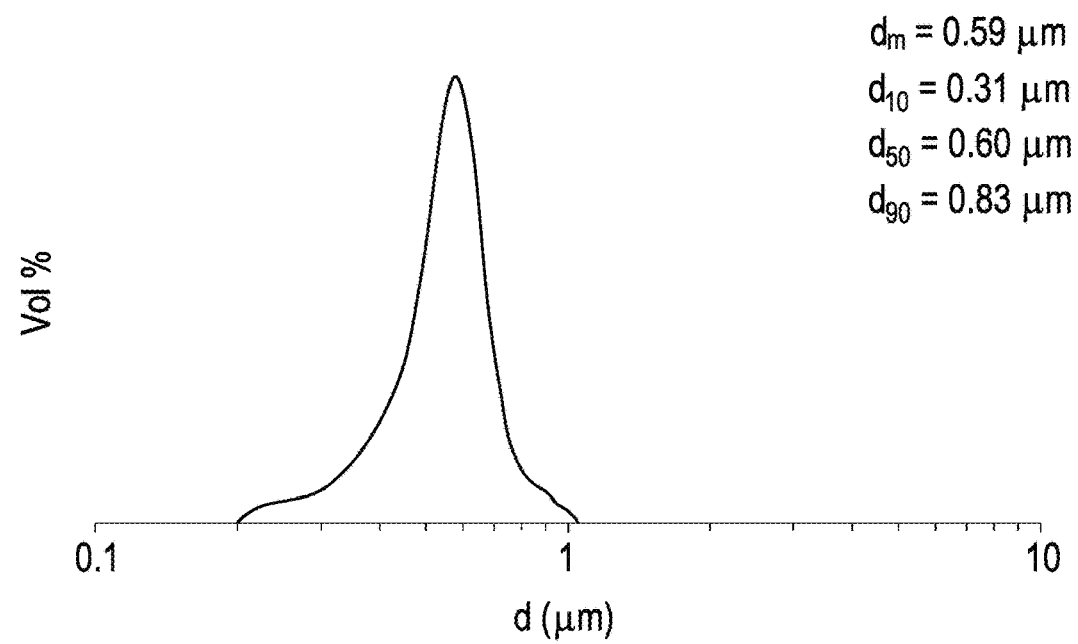

FIG. 2A shows the dimensional distribution of a representative sample of particles of submicrometric powder according to the invention (2d1) prepared as described in example 2A, evaluated by DLS. The chart represents the Volume % (Vol %) of the particles as a function of diameter (d) measured in micron (μm). The particles have a mean diameter $(d_m)=0.52$ μm, 10% of the particles having diameter $d_{10}=0.28$ μm; 50% of the particles having diameter $d_{50}=0.54$ μm; and 90% of the particles having diameter $d_{90}=0.72$ μm.

FIG. 2A' shows the dimensional distribution of the same sample of submicrometric powder of FIG. 2A, evaluated by DLS after 30 days of preservation in accelerated stability conditions. The chart represents the Volume % (Vol %) of the particles as a function of diameter (d) measured in micron (μm). The particles have a mean diameter $(d_m)=0.59$ μm, 10% of the particles having diameter $d_{10}=0.31$ μm; 50% of the particles having diameter $d_{50}=0.60$ μm; and 90% of the particles having diameter $d_{90}=0.83$ μm.

Figure 2B:
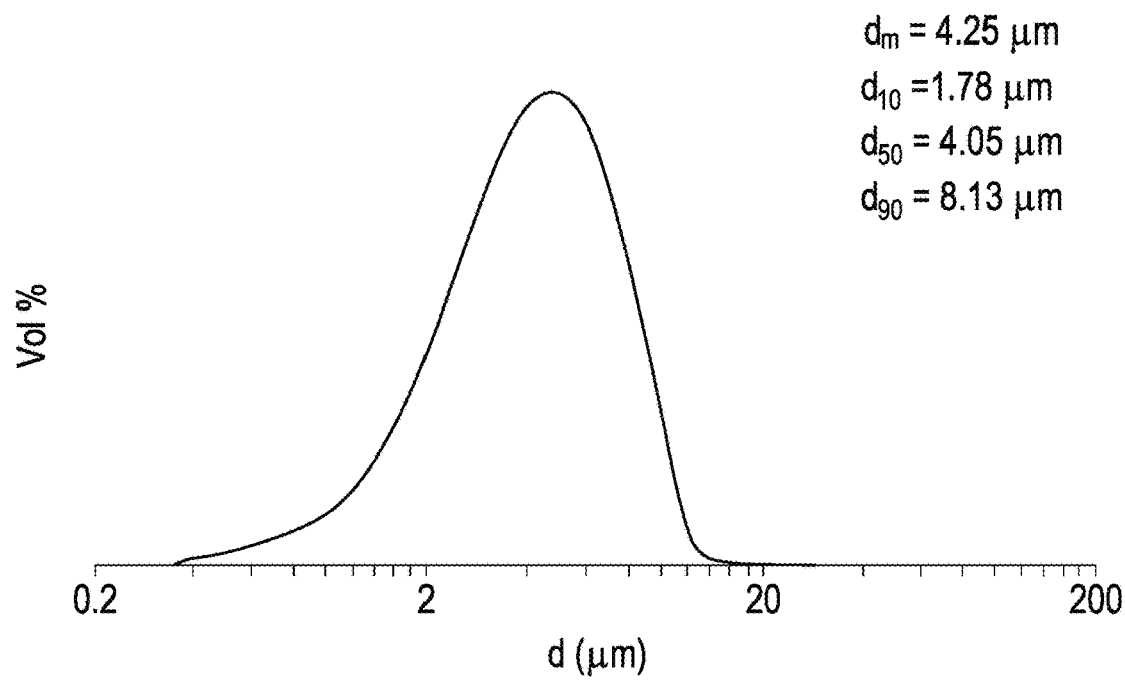

FIG. 2B shows the dimensional distribution of a representative sample of particles of micrometric powder according to the invention (2d2) prepared as described in example 2B, evaluated by LS. The chart represents the Volume % (Vol %) of the particles as a function of diameter (d) measured in micron (μm). The particles have a mean diameter $(d_m)=4.25$ μm, 10% of the particles having diameter $d_{10}=1.78$ μm; 50% of the particles having diameter $d_{50}=4.05$ μm; and 90% of the particles having diameter $d_{90}=8.13$ μm.

Figure 2C:
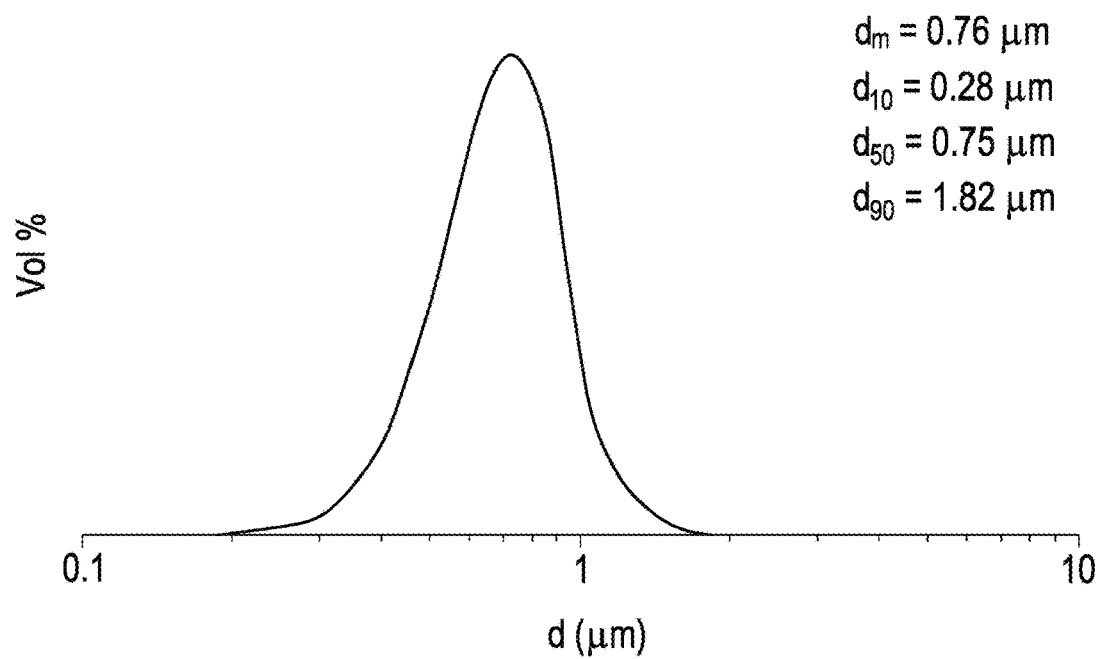
Figure 2C:
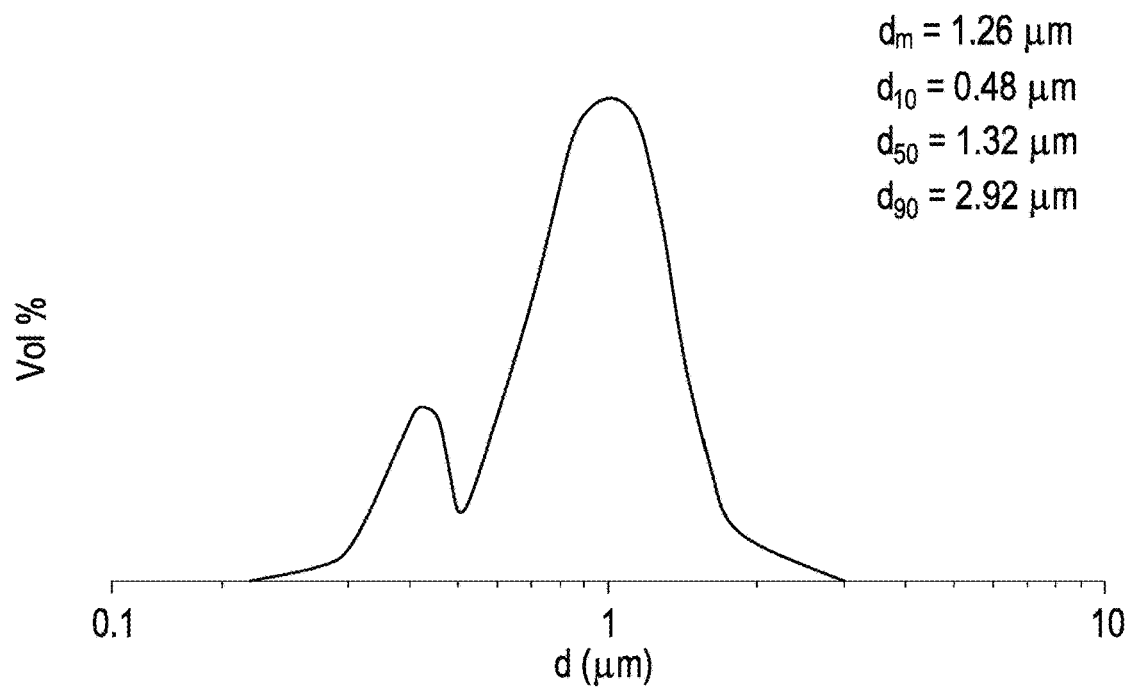

FIG. 2C shows the dimensional distribution of a representative sample of comparison particles of submicrometric powder (2b1) prepared as described in example 2A, evaluated by DLS. The chart represents the Volume % (Vol %) of the particles as a function of diameter (d) measured in micron (μm). The particles have a mean diameter $(d_m)=0.76$ μm, 10% of the particles having diameter $d_{10}=0.28$ μm; 50% of the particles having diameter $d_{50}=0.75$ μm; and 90% of the particles having diameter d90=1.82 μm.

FIG. 2C' shows the dimensional distribution of the same sample of submicrometric powder of FIG. 2C, evaluated by DLS after 30 days of preservation in accelerated stability conditions. The chart represents the Volume % (Vol %) of the particles as a function of diameter (d) measured in micron (μm). The particles have a mean diameter $(d_m)=1.26$ μm, 10% of the particles having diameter $d_{10}=0.48$ μm; 50% of the particles having diameter $d_{50}=1.32$ μm; and 90% of the particles having diameter $d_{90}=2.92$ μm.

Figure 2D:
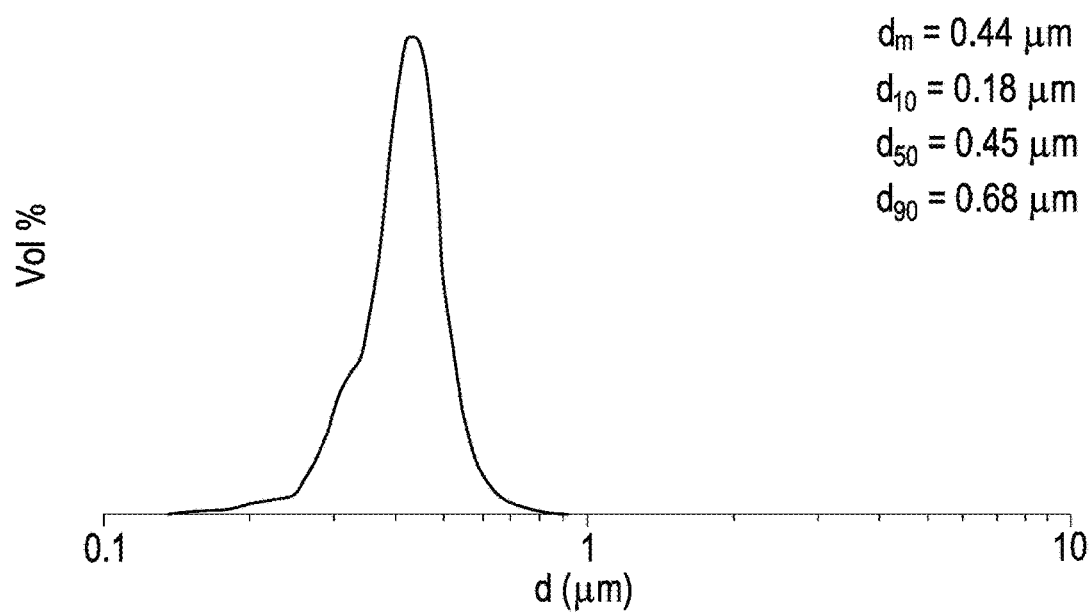

FIG. 2D shows the dimensional distribution of a representative sample of particles of submicrometric powder according to the invention (2d'1) prepared as described in example 2A', evaluated by DLS. The chart represents the Volume % (Vol %) of the particles as a function of diameter (d) measured in micron (μm). The particles have a mean diameter $(d_m)=0.44$ μm, 10% of the particles having diameter $d_{10}=0.18$ μm; 50% of the particles having diameter $d_{50}=0.45$ μm; and 90% of the particles having diameter $d_{90}=0.68$ μm.

Figure 2E:
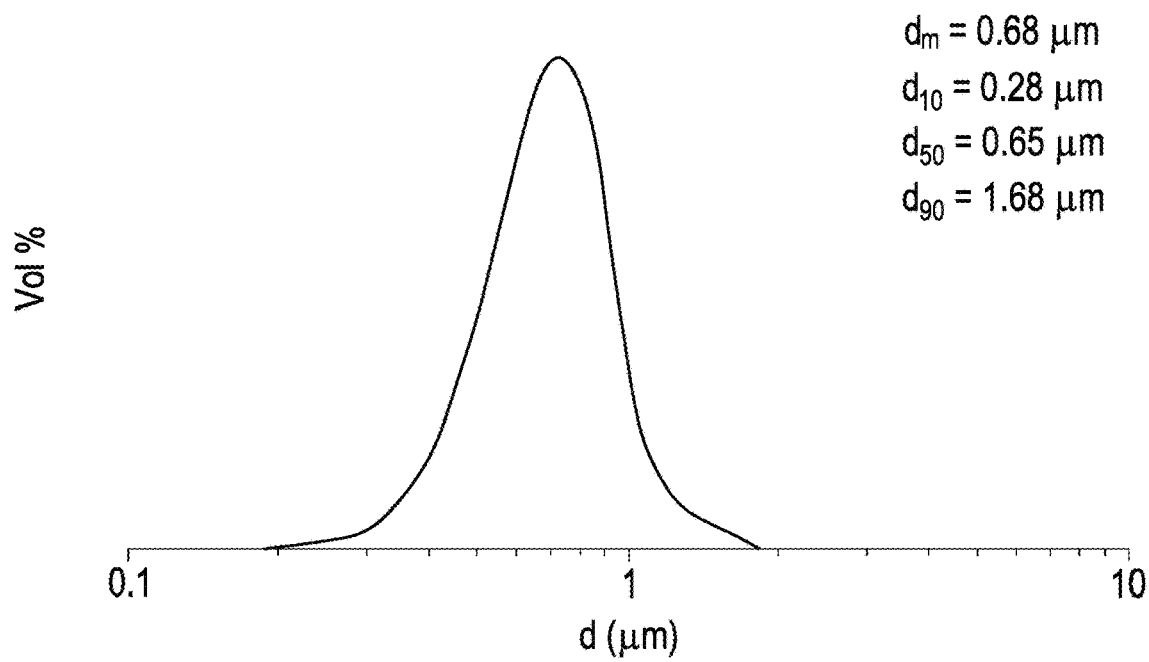

FIG. 2E shows the dimensional distribution of a representative sample of particles of submicrometric powder according to the invention (2d"1) prepared as described in example 2A', evaluated by DLS. The chart represents the Volume % (Vol %) of the particles as a function of diameter (d) measured in micron (µm). The particles have a mean diameter $(d_m)=0.68$ µm, 10% of the particles having diameter $d_{10}=0.28$ µm; 50% of the particles having diameter $d_{50}=0.65$ µm; and 90% of the particles having diameter $d_{90}=1.68$ µm.

Figure 2F:
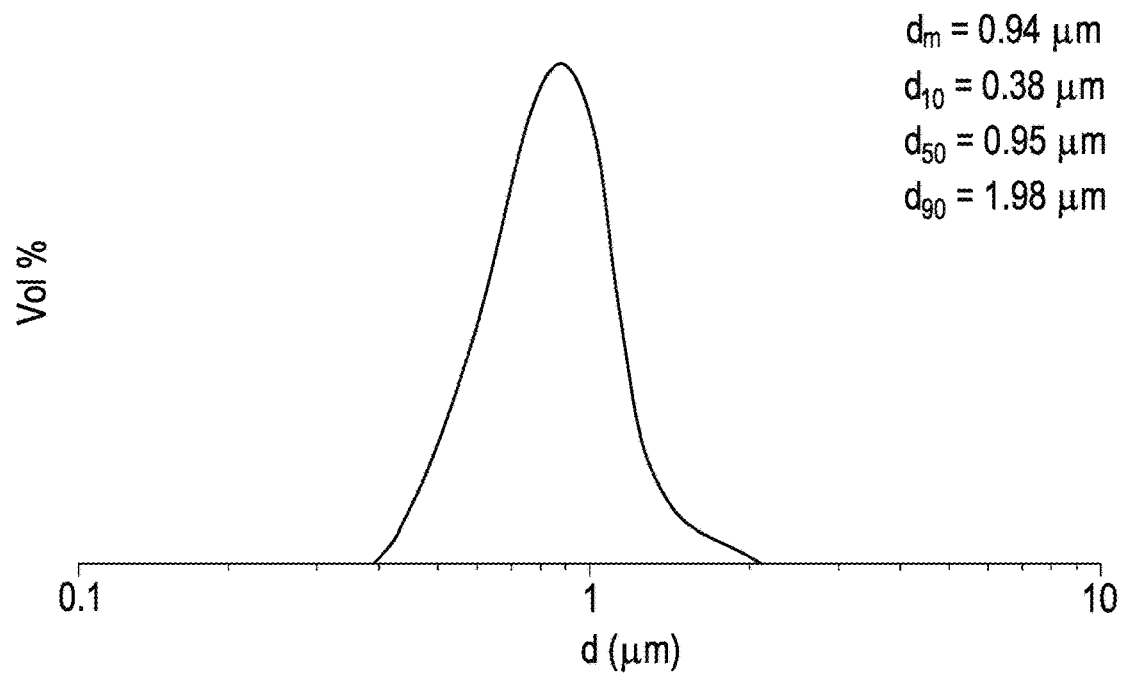

FIG. 2F shows the dimensional distribution of a representative sample of comparison particles of submicrometric powder (2d'''1) prepared as described in example 2A', evaluated by DLS. The chart represents the Volume % (Vol %) of the particles as a function of diameter (d) measured in micron (µm). The particles have a mean diameter $(d_m)=0.94$ µm, 10% of the particles having diameter $d_{10}=0.38$ µm; 50% of the particles having diameter $d_{50}=0.95$ µm; and 90% of the particles having diameter $d_{90}=1.98$ µm.

Figure 3A:
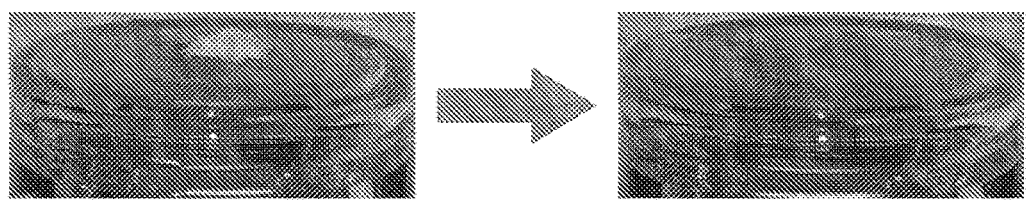

FIG. 3A shows the photographic images acquired at time zero (a) and after five minutes (b) of a representative sample of the submicrometric powder of the invention (2d1) prepared as described in example 2A, placed in contact with Simulated Wound Fluid (SWF).

Figure 3B:
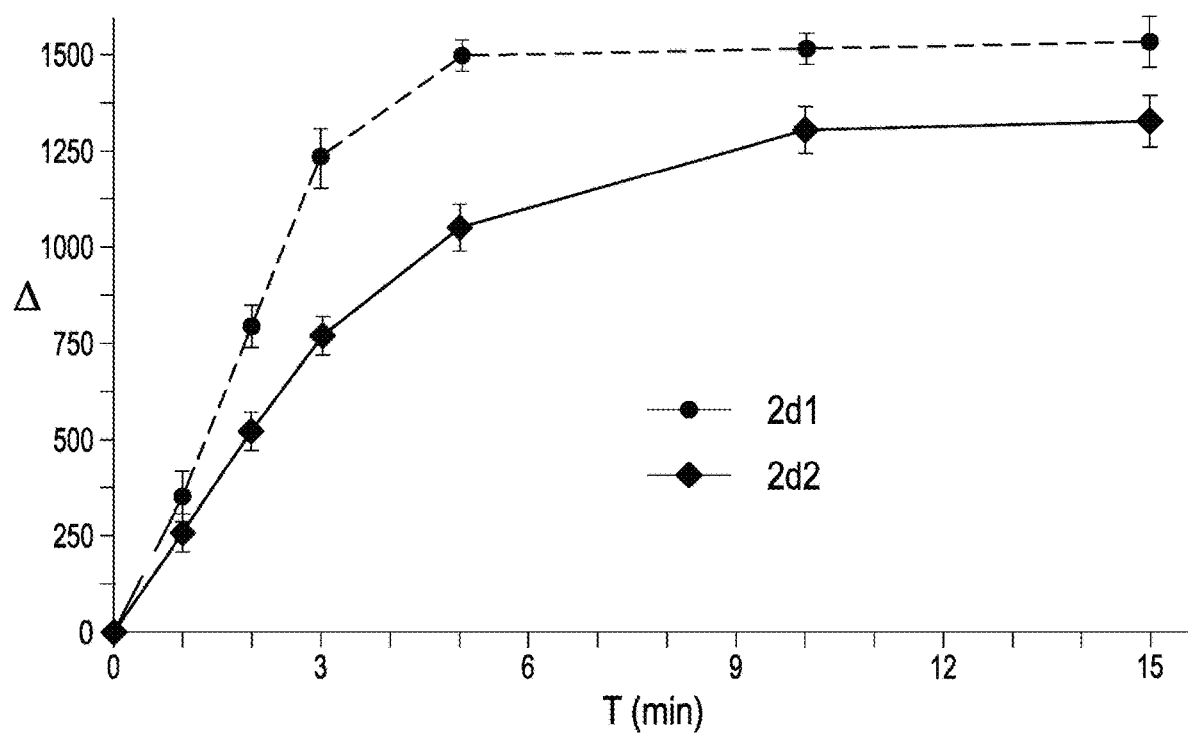

FIG. 3B shows the capacity to absorb exudate by two representative samples of powder of the invention, i.e. the submicrometric powder (2d1) and the micrometric powder (2d2), prepared respectively as described in example 2A and 2B. The chart represents the % increase of the weight of the dry powder as a result of gelification (Δ) as a function of time (t), measured in minutes.

The chart further shows that the complete gelification of the submicrometric powder (2d1) and of the micrometric powder (2d2) takes place respectively in approximately 3-5 minutes and 5-10 minutes.

Figure 3C:
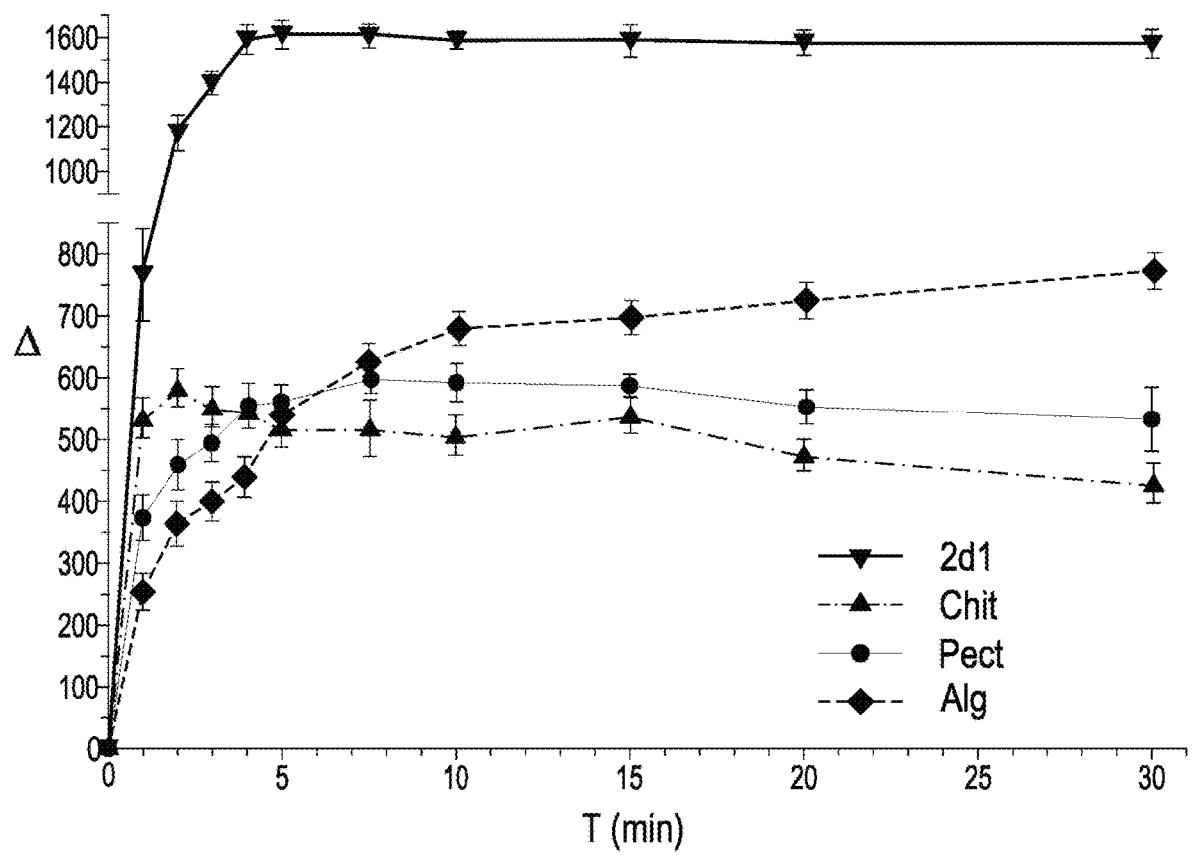

FIG. 3C shows the capacity to absorb exudate by a representative sample of powder of the invention, i.e. the submicrometric powder (2d1) prepared as described in example 2A, in comparison with a sample of powder of alginate (Alg) only, pectin (Pect) only, chitosan (Chit) only. The chart represents the % increase of the weight of the dry powder as a result of gelification (Δ) as a function of time (t), measured in minutes.

Figure 4A:
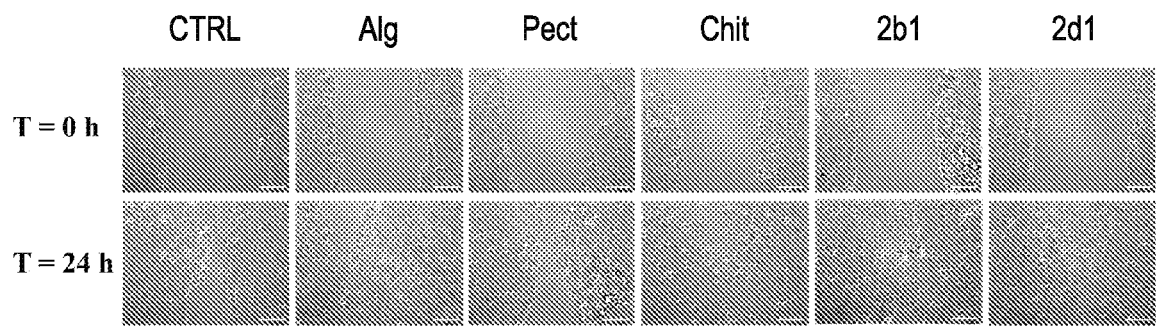

FIG. 4A shows an image representative of each group of cells: untreated (CTRL), or treated with alginate (Alg) only, pectin (Pect) only, chitosan (Chit) only, composition in submicrometric powder form (2b1) (Alg/Pect), composition in submicrometric powder form (2d1) (Alg/Pect/Chit) acquired in the microscope by means of a 10× lens during the experiment described in example 8 at time 0 and 24 hours after the creation of the lesion of the cell monolayer.

Figure 4B:
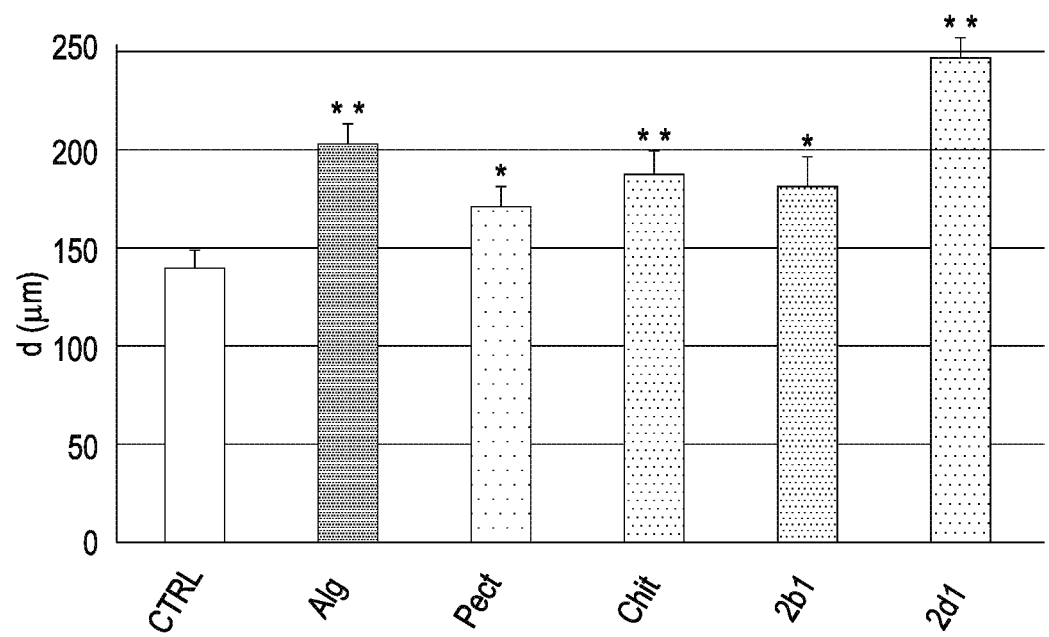

FIG. 4B shows the cell migration rate, expressed as distance (d) in micrometres (µm) travelled in 24 hours, of each group of cells: untreated (CTRL), or treated with alginate (Alg) only, pectin (Pect) only, chitosan (Chit) only, composition in submicrometric powder form (2b1) (Alg/Pect), composition in submicrometric powder form (2d1) (Alg/Pect/Chit) as described in example 8. The chart represents the distance (d) measured in micron (µm) between the two edges of the wound as a function of the type of treatment. A value of $P<0.05$ was considered to indicate a statistically significant difference.

Figure 5:
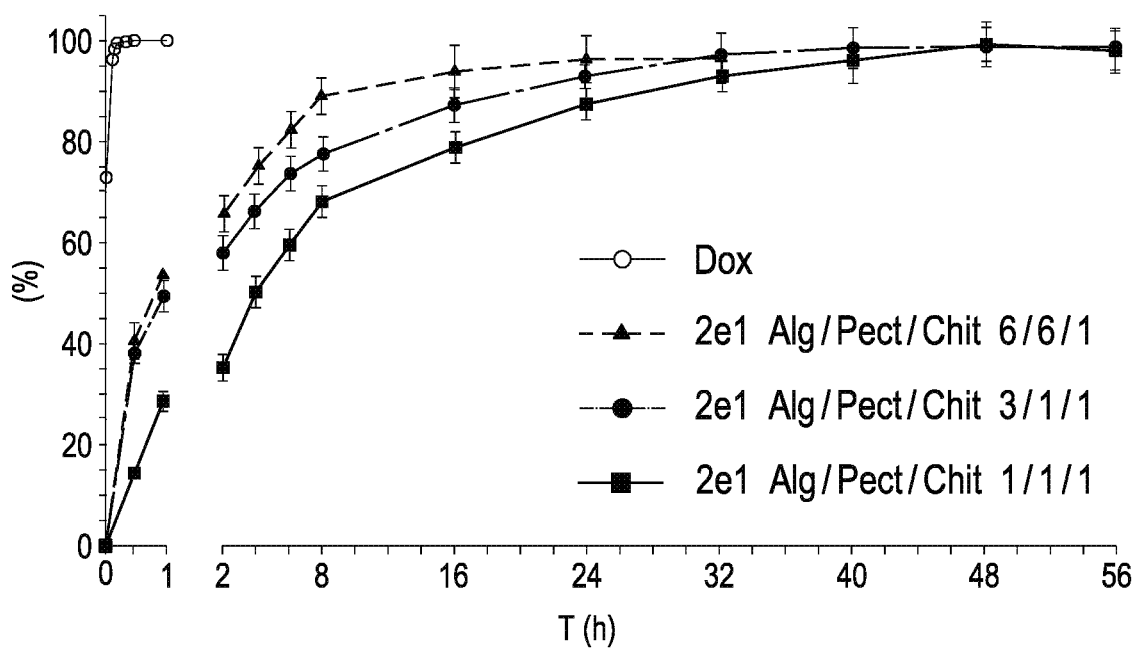

FIG. 5 shows the doxycycline release from the composition in submicrometric powder form (2e1) in which the weight ratio Alg/Pect/Chit is 6/6/1 and from compositions in submicrometric powder form in which the weight ratio is respectively 3/1/1 and 1/1/1. As comparison, a powder consisting of only doxycycline hyclate (Dox) was used. The chart represents the percentage of doxycycline released (%) as a function of time (hour).

Figure 6B:
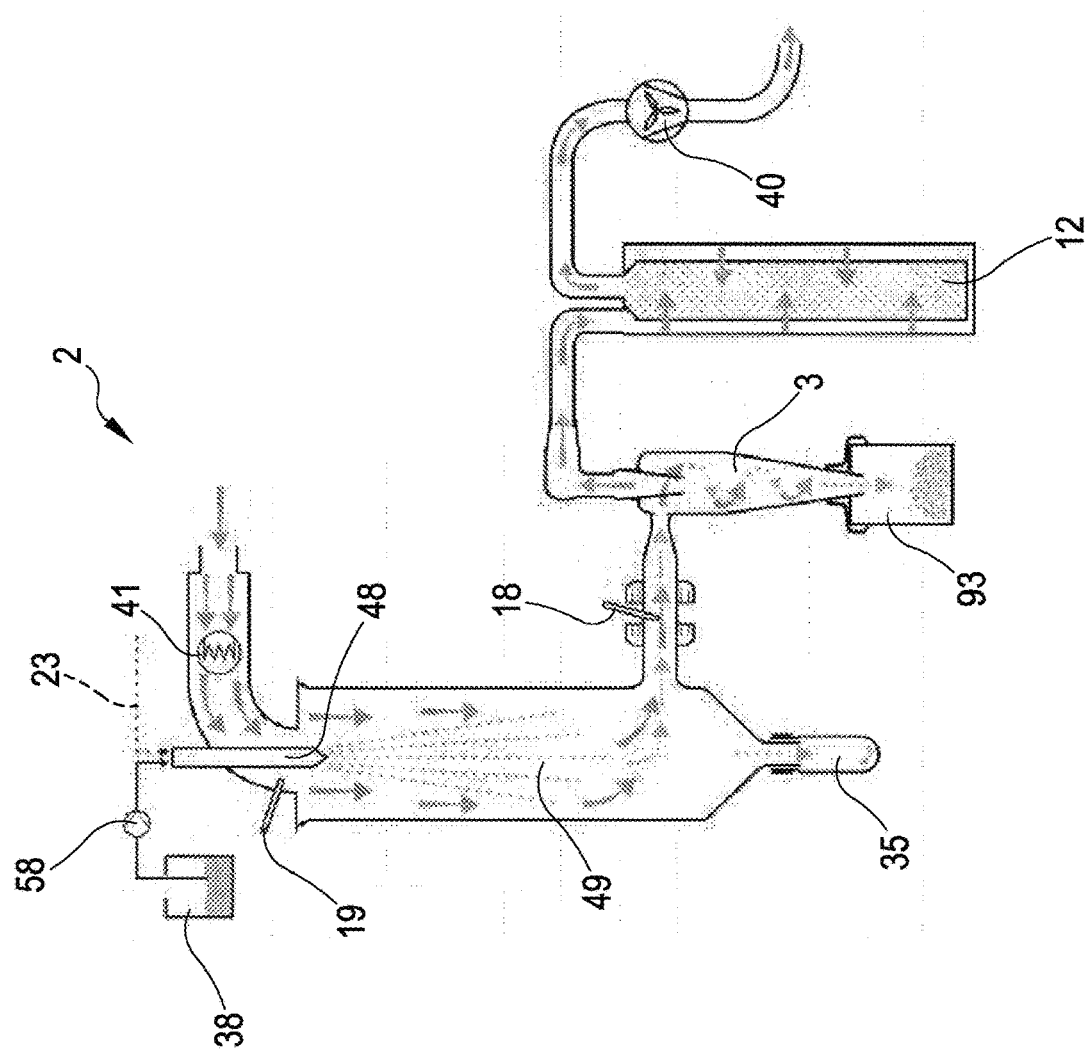
Figure 6A:
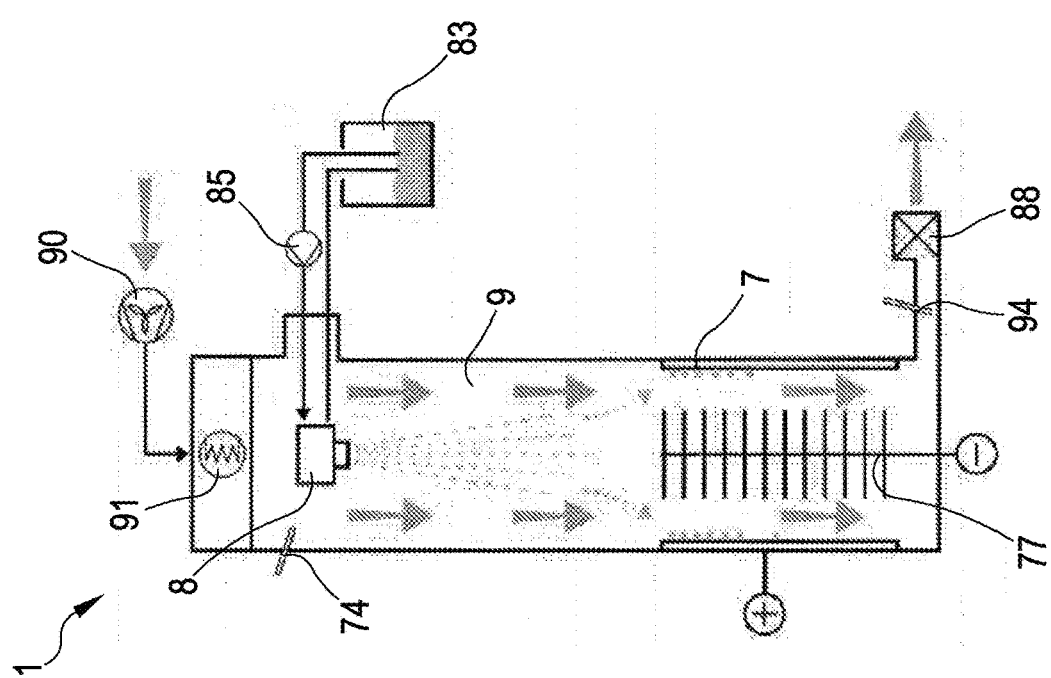

FIG. 6A shows a functional diagram of the apparatus used in example 2A for the preparation of the compositions in submicrometric powder form.

FIG. 6B shows a functional diagram of the apparatus used in example 2B for the preparation of the compositions in micrometric powder form.

Figure 7A:
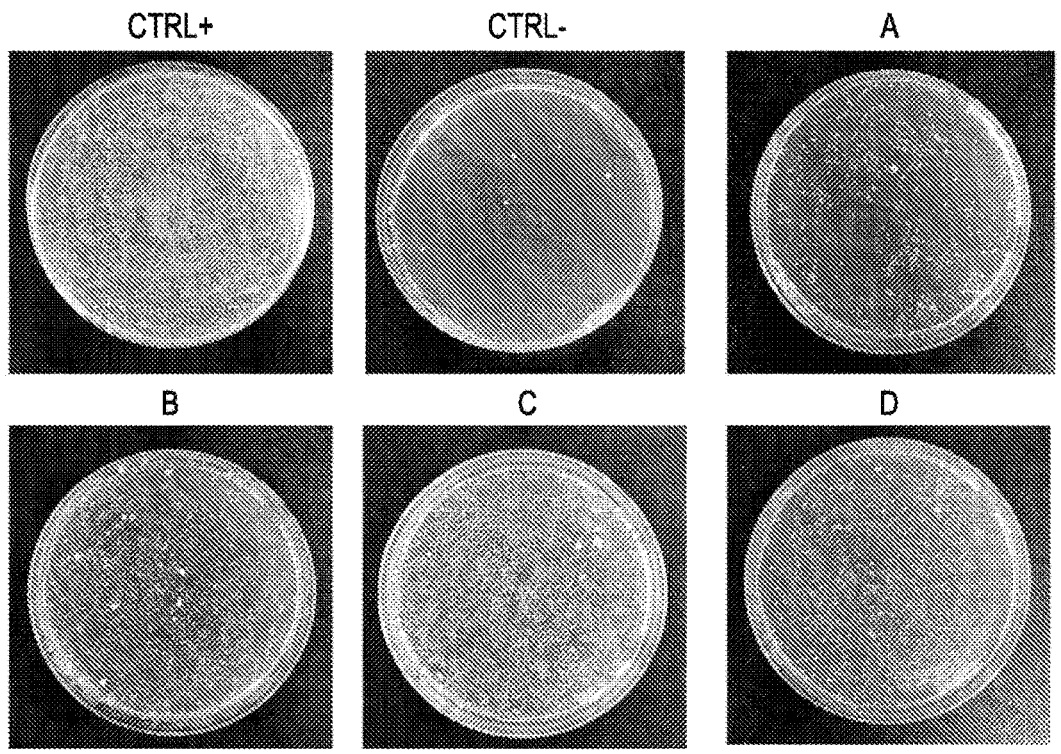

FIG. 7A shows a representative image of each group: untreated meat (CTRL+), powder (2d1) (CTRL−), meat+powder (2d1) 200:1 weight/weight (A), meat+powder (2d1) 300:1 weight/weight (B), meat+powder (2d1) 400:1 weight/weight (C), and meat+powder (2d1) 500:1 weight/weight (D) acquired with the microscope by a 2.5× lens during the experiment described in example 10, after 8 days of incubation at 4° C.

Figure 7B:
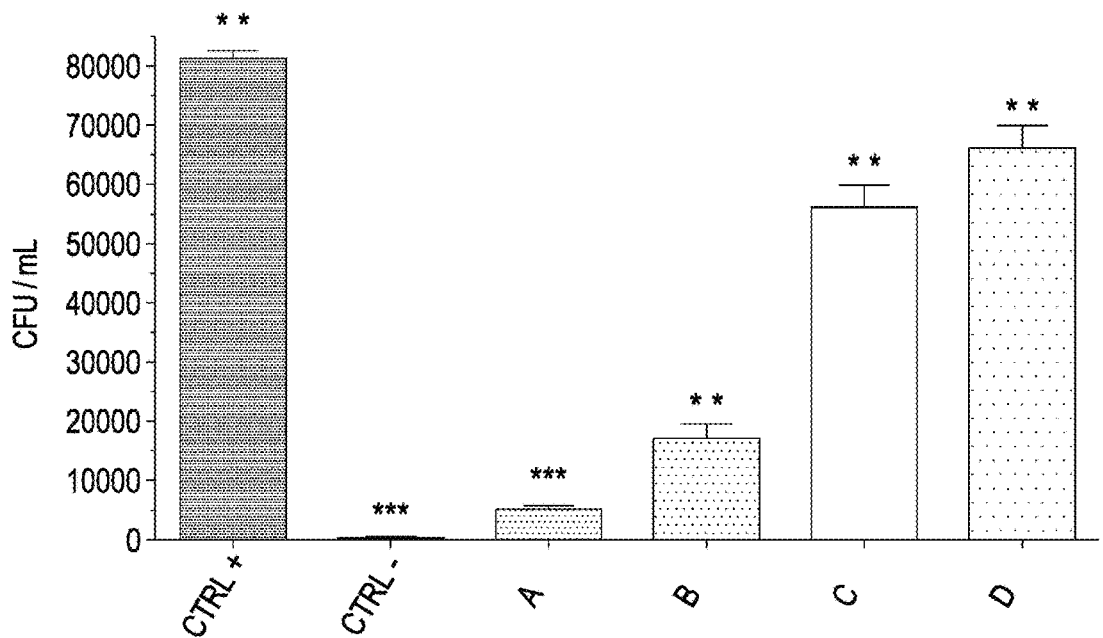

FIG. 7B shows the microbial charge, expressed as CFU/mL of each group: untreated meat (CTRL+), powder (2d1) (CTRL−), meat+powder (2d1) 200:1 weight/weight (A), meat+powder (2d1) 300:1 weight/weight (B), meat+powder (2d1) 400:1 weight/weight (C), and meat+powder (2d1) 500:1 weight/weight (D). The values of $P<0.01$ and $P<0.005$ were considered to indicate a statistically significant difference.

DETAILED DESCRIPTION OF THE INVENTION

Polysaccharides constitute a class of organic chemical compounds characterised by a large number of repetitive units, bonded together to form large, complex molecules. Chemically, polysaccharides are divided into: homopolysaccharides, whose chemical structure is a polymeric repetition of a single monosaccharide unit; an important homopolysaccharide is, for example, glycogen; and heteropolysaccharides, i.e. composed from the union of multiple different monosaccharides, by means of glycosidic bonds. An example of heteropolysaccharides are glycosaminoglycans, consisting of dimers (i.e. pairs) of different monosaccharides, which repeat in polymeric sequences.

Alginic acid and sodium alginate are natural polysaccharides obtained from brown algae consisting of two monomers, guluronic acid and mannuronic acid.

Pectin, extracted from fruit, for example from citrus peel, is a heteropolysaccharide composed by the union of multiple different monosaccharides. The structure of one of the most widely known pectins is based on a chain of units of galacturonic acid bonded by alfa bonds (1-4); other saccharide units can also be present in pectin, for example xylose, apiose, rhamnose, galactose, arabinose.

The degree of amidation (DA) of the pectin is defined as the percentage of amidated units of galacturonic acid with respect to the total units of galacturonic acid present in the pectin molecule.

The degree of methoxylation (DM) of the pectin is defined as the percentage of methoxylated units of carboxyl groups with respect to the total units of carboxyl groups present in the pectin molecule.

Chitosan is a natural substance obtained from chitin, present for example in the shell of crustaceans. Chitosan is a linear polysaccharide composed by D-glucosamine and N-acetyl-D-glucosamine, bonded by beta bonds (1-4).

As used herein, the term "treating" or "treatment" referred to cutaneous wounds means establishing a process of partial or total healing of the wound and/or reducing partially or totally the infection of the wound. In the preferred embodiment, the treatment of a patient affected by a cutaneous wound means the complete healing of a wound.

As used herein, the term "effective quantity" is the quantity of composition in powder form that, when applied to a patient, is effective for establishing a process of partial or total healing of a wound.

Therefore, a first object of the invention is a composition in powder form comprising the following polysaccharides
- alginic acid or sodium alginate,
- pectin,
- chitosan,
wherein the % by weight of the polysaccharides is at least 20% with respect to the total weight of the powder.

Preferably, the composition according to the first object of the invention comprises
- alginic acid or sodium alginate between 10% and 60% by weight,
- pectin between 10% and 60% by weight,
- chitosan between 5% and 70% by weight
with respect to the total weight of the polysaccharides.

A second object of the invention is a composition in liquid solution or suspension form comprising the following polysaccharides
- alginic acid or sodium alginate,
- pectin,
- chitosan.

Preferably, the composition according to the first or to the second object of the invention comprises
- alginic acid or sodium alginate between 15% and 60% by weight,
- pectin between 15% and 60% by weight,
- chitosan between 5% and 70% by weight
with respect to the total weight of the polysaccharides.

Preferably, in the composition according to the first or to the second object of the invention the alginic acid or the sodium alginate has a high content of residues of mannuronic acid, for example a content of residues of mannuronic acid greater than or equal to 55%, preferably greater than 60%; preferably comprised between 55% and 75%, more preferably comprised between 60% and 73% by weight with respect to the total weight of the alginic acid or of the sodium alginate, respectively.

Preferably, in the composition according to the first or to the second object of the invention pectin is amidated, for example it has a degree of amidation (DA) greater than or equal to 2%, preferably greater than 3%; preferably comprised between 2% and 30%, more preferably comprised between 3% and 25%.

Preferably, in the composition according to the first or to the second object of the invention pectin has a low degree of methoxylation (DM), for example lower than or equal to 48%, preferably lower than 40%; preferably comprised between 20% and 48%, more preferably comprised between 25% and 40%.

Preferably, in the composition according to the first or to the second object of the invention chitosan has low molecular weight, for example lower than or equal to 400000 Da; preferably lower than 200000 Da; preferably comprised between 15000 Da and 400000 Da, more preferably comprised between 50000 Da e 200000 Da.

Optionally, the composition according to the first or to the second object of the invention can also comprise at least an additional polysaccharide, for example, dextran, α- and β-glycans, carrageenan, heparin, hyaluronic acid or sodium hyaluronate.

In an embodiment according to the first or to the second object of the invention, the additional polysaccharide is preferably hyaluronic acid or sodium hyaluronate, more preferably from 0.1% to 10% by weight with respect to the total weight of the polysaccharides.

Optionally, the composition according to the first or to the second object of the invention can also comprise at least one ingredient selected from: soothing agents, cicatrizing agents, growth factors, peptides, anti-inflammatory agents and antimicrobials, alone or in combination.

Soothing agents according to the first or to the second object of the invention are for example: aloe vera extract or calendula extract.

Suitable cicatrizing agents according to the first or to the second object of the invention are for example histidine, rutin, vitamin A, B-group vitamins.

Suitable growth factors according to the first or to the second object of the invention are for example the nerve growth factor (NGF), vascular endothelial growth factor (VEGF) or the epidermal growth factor (EGF).

Suitable peptides according to the first or to the second object of the invention are for example the N-terminal peptide derived from Annexin A1 (Ac2-26) or antimicrobial peptides (AMP).

Suitable anti-inflammatory agents according to the first or to the second object of the invention are for example non-steroidal anti-inflammatory agents such as propionic acid derivatives such as ketoprofen, oxicams such piroxicam, steroidal anti-inflammatory agents such as betamethasone or pharmaceutically acceptable salts thereof.

Suitable antimicrobial agents according to the first or to the second object of the invention are for example aminoglycoside antibiotics such as gentamicin, lincosamides such as clindamycin, macrolides such as clarithromycin, quinolones such as levofloxacin, tetracyclines such as doxycycline or pharmaceutically acceptable salts thereof.

More preferably, the composition according to the first or to the second object of the invention comprises
- 25%-60% by weight of sodium alginate,
- 25%-60% by weight of pectin,
- 5%-50% by weight of chitosan
with respect to the total weight of the polysaccharides.

More preferably, the composition according to the first or to the second object of the invention comprises
- 30%-50% by weight of sodium alginate,
- 30%-50% by weight of pectin,
- 5%-20% by weight of chitosan
with respect to the total weight of the polysaccharides.

Still more preferably, the composition according to the first or to the second object of the invention comprises
- 30%-50% by weight of sodium alginate
- 30%-50% by weight of pectin,
- 5%-20% by weight of chitosan
with respect to the total weight of the polysaccharides, in which
- the % by weight of mannuronic acid of the sodium alginate is between 55% and 75% with respect to the total weight of sodium alginate;
- the degree of amidation (DA) of the pectin is between 2% and 30% and/or its degree of methoxylation (DM) is between 20% and 48%;
- chitosan has a molecular weight between 15000-400000 Da.

In a preferred embodiment, the composition according to the first or to the second object of the invention comprises
- 40%-50% by weight of sodium alginate
- 40%-50% by weight of pectin,
- 5%-15% by weight of chitosan
with respect to the total weight of the polysaccharides, in which the % by weight of mannuronic acid of the sodium alginate is between 55% and 75% with respect to the total weight of sodium alginate;

the degree of amidation (DA) of the pectin is between 2% and 30% and/or its degree of methoxylation (DM) is between 20% and 48%;

chitosan has a molecular weight between 15000-400000 Da.

In an embodiment, the composition according to the first or to the second object of the invention consists of 46% by weight of sodium alginate
46% by weight of pectin,
7% by weight of chitosan with respect to the total weight of the polysaccharides, in which the % by weight of mannuronic acid of the sodium alginate is between 55% and 75% with respect to the total weight of sodium alginate;

the degree of amidation (DA) of the pectin is between 2% and 30% and/or its degree of methoxylation (DM) is between 20% and 48%;

chitosan has a molecular weight between 15000-400000 Da.

In another embodiment, the composition according to the first or to the second object of the invention comprises 40%-50% by weight of sodium alginate
40%-50% by weight of pectin,
5%-15% by weight of chitosan
0.1%-3% by weight of hyaluronic acid or sodium hyaluronate with respect to the total weight of the polysaccharides, in which the % by weight of mannuronic acid of the sodium alginate is between 55% and 75% with respect to the total weight of sodium alginate;

the degree of amidation (DA) of the pectin is between 2% and 30% and/or its degree of methoxylation (DM) is between 20% and 48%;

chitosan has a molecular weight between 15000-400000 Da.

In another embodiment, the composition according to the first or to the second object of the invention consists of 26% by weight of sodium alginate
26% by weight of pectin,
47% by weight of chitosan with respect to the total weight of the polysaccharides, in which the % by weight of mannuronic acid of the sodium alginate is between 55% and 75% with respect to the total weight of sodium alginate;

the degree of amidation (DA) of pectin is between 2% and 30% and/or its degree of methoxylation (DM) is between 20% and 48%;

chitosan has a molecular weight between 15000-400000 Da.

Optionally said preferred embodiments can also comprise at least one antimicrobial ingredient, preferably doxycycline or a pharmaceutically acceptable salt thereof.

Preferably in the composition according to the first or to the second object of the invention, taking as reference chitosan equal to 1, the weight ratio between alginic acid or sodium alginate/pectin/chitosan is between 0.20/0.20/1 and 10/10/1, preferably it is between 0.75/0.75/1 and 10/10/1, preferably it is selected between 0.55/0.55/1, 3/3/1 and 6/6/1.

Optionally, the composition according to the first or to the second object of the invention can also comprise at least one inorganic salt selected from: sodium carbonate and sodium or potassium bicarbonate; more preferably sodium bicarbonate.

Preferably the composition according to the first or second object of the invention comprises between 2.5% and 30% weight/weight of at least one inorganic salt with respect to the total weight of the polysaccharides; more preferably between 2.5% and 30% weight/weight of sodium bicarbonate with respect to the total weight of the polysaccharides.

Preferably according to the first object of the invention in the composition in powder form the % by weight of polysaccharides is at least 30%, at least 40%, at least 50%, at least 60%, at least 70%, at least 80%, at least 90%, at least 95%, at least 97%, at least 99.9% with respect to the total weight of the powder.

According to the first object of the invention, in the composition in powder form the % by weight of at least one soothing agent, cicatrizing agent, growth factor, peptide, anti-inflammatory or antimicrobial is between 0.01% and 5% with respect to the total weight of the powder.

According to the first object of the invention, in the composition in powder form the quantity of at least one soothing agent, cicatrizing agent, growth factor, peptide, anti-inflammatory or antimicrobial is between 0.01 µg and 2 mg.

In a preferred embodiment according to the first object of the invention, the composition in powder form consists of 100% by weight of polysaccharides with respect to the total weight of the powder.

In a still more preferred embodiment according to the first object of the invention the composition according to the first object of the invention comprises at least 30%, at least 40%, at least 50%, at least 60%, at least 70%, at least 80%, at least 90%, at least 95%, at least 97%, at least 99.9%, is constituted by 100% of polysaccharides with respect to the total weight of the powder and consists of 46% by weight of sodium alginate
46% by weight of pectin,
7% by weight of chitosan with respect to the total weight of the polysaccharides, in which the % by weight of mannuronic acid of the sodium alginate is between 55% and 75% with respect to the total weight of sodium alginate;

the degree of amidation (DA) of the pectin is between 2% and 30%, and its degree of methoxylation (DM) is between 20% and 48%;

chitosan has a molecular weight between 15000-400000 Da.

In another still more preferred embodiment according to the first object of the invention the composition according to the first object of the invention comprises at least 30%, at least 40%, at least 50%, at least 60%, at least 70%, at least 80%, at least 90%, at least 95%, at least 97%, at least 99.9%, is constituted by 100% of polysaccharides with respect to the total weight of the powder and consists of 26% by weight of sodium alginate
26% by weight of pectin,
47% by weight of chitosan with respect to the total weight of the polysaccharides, in which the % by weight of mannuronic acid of the sodium alginate is between 55% and 75% with respect to the total weight of sodium alginate;

the degree of amidation (DA) of the pectin is between 2% and 30%, and its degree of methoxylation (DM) is between 20% and 48%;

chitosan has a molecular weight between 15000-400000 Da.

According to the first object of the invention, the composition in powder form has a particle diameter between 100 nm and 5 micron, preferably between 200 nm and 2.5 micron, still more preferably between 400 nm and 800 nm.

Preferably, according to the second object of the invention in the composition in liquid solution, or suspension, form the total concentration of the polysaccharides is at least 0.25% w/v, preferably at least 0.40% w/v; preferably, it is between 0.25% and 5.0% w/v, more preferably it is between 0.40% and 1.5% w/v.

Preferably, according to the second object of the invention the composition is in the form of an aqueous or hydroalcoholic, ethanol or isopropanol based, solution or suspension.

Preferably according to the second object of the invention, the hydroalcoholic solution is from 2.5% to 25% volume/volume; more preferably, 5% volume/volume.

A third object of the invention is the composition in powder form as defined in the first object of the invention, for use as a medicament.

A fourth object of the invention is the composition in powder form as defined in the first object of the invention, for use in the treatment of cutaneous wounds.

A fifth object of the invention is a method for treating a cutaneous wound in a patient by the application to said wound of a composition in powder form as defined in the first object of the invention, in an effective quantity to treat such wound.

Preferably in the method according to the fifth object of the invention the effective quantity to treat such a wound is between 5 mg/cm$^2$ and 25 mg/cm$^2$ of the lesion.

A sixth object of the invention is the use of the composition in powder form as defined in the first object of the invention, for application to cutaneous wounds, preferably as a medical device.

In an embodiment of the fourth, fifth or sixth object of the invention, the composition does not contain at least one ingredient selected from: soothing agents, cicatrizing agents, growth factors, peptides, anti-inflammatory agents and antimicrobials.

In an embodiment of the fourth, fifth or sixth object of the invention, the composition also contains at least one ingredient selected from: soothing agents, cicatrizing agents, growth factors, peptides, anti-inflammatory agents and antimicrobials.

It is well known that keratinocytes, being the largest group of cells within the skin, are able to start an intense mitotic activity along the edges of the wound. One or two days after the lesion, the same keratinocytes, stimulated by the local release of growth factor, proliferate and migrate inside the wound. Cell migration is a step that requires the presence of a fluid environment and consists of different stage controlled by a chemotactic gradient generated by the growth factors. In the absence of a hydrated surface, the keratinocytes secrete proteolytic enzymes that dig deeply in the wound bed, in the attempt to reach a level of humidity suitable for the migratory process. First of all, the keratinocytes separate from each other and adhere to the cells of the basement membrane, undergoing, during the migration, a transformation that sees their extension in the direction in which tissue growth is needed. Only when the cells touch each other from one part of the wound to the other, is the migration process interrupted as a result of the mechanism known as "contact inhibition". When the cutaneous surface is completely covered by new endothelial cells, the wound can be considered closed.

As will be discussed in greater depth in the experimental part, the composition of the invention induces the cell migration of the keratinocytes and therefore its use in powder form for example as a medical device represents an important aid in the wound healing process.

A seventh object of the invention is the process for preparing the composition in powder form as defined in the first object of the invention by an atomization process.

According to the seventh object of the invention, the atomisation process can take place according to techniques known to the person skilled in the art, such as spray drying as described in De Cicco F et al, (2014), Carbohydrate Polymers 101:1216-1224; or by supercritical assisted atomization (SAA) as described in Aquino R P et al, (2013) International Journal of Pharmaceutics 440: 188-194 or in De Cicco F et al, (2014), Carbohydrate Polymers 101:1216-1224; or by nanospray drying technology, as described in De Cicco et al, (2014), International Journal of Pharmaceutics 473: 30-37.

Preferably according to the seventh object of the invention, the process of atomization of the composition in liquid solution, or suspension, form to yield the corresponding composition in powder form, takes place by spray drying technology employing in general terms the procedure described in De Cicco et al, (2014), International Journal of Pharmaceutics 473: 30-37, for obtaining powders constituted by submicrometric particles and the procedure described in De Cicco F et al, (2014), Carbohydrate Polymers 101:1216-1224 for obtaining micrometric powders, but utilising specific operating parameters. Use of the specific composition of the invention advantageously allows to reduce the inlet temperature of the composition in the atomization chamber with respect to the prior art referenced above.

Therefore, preferably according to the seventh object of the invention, the atomization process for preparing the composition in powder form as defined in the first object of the invention takes place by spray drying technology utilising the following operating parameters:

Inlet temperature of the composition in liquid solution, or suspension, form according to the second object of the invention comprised between 50° C. and 110° C., preferably between 50° C. and 100° C., still more preferably between 50° C. and 60° C.;

Atomizer feeding rate between 7.5 and 20 ml/min, preferably 9.5 ml/min;

Diameter of the atomization nozzle between 3.0 and 500 microns, preferably 4.0 micron;

Incoming air flow between 100 L/min and 600 L/min, preferably 100 L/min;

Pressure in drying chamber comprised between 38 mbar and 60 mbar, preferably 38 mbar;

Relative spray rate comprised between 50 and 100%, preferably 100%.

The functional diagram of the apparatus used for the preparation of the composition in powder form by Nano Spray and Mini Spray technology is shown respectively in FIGS. 6A and 6B.

FIG. 6A shows, by way of non-limiting explanation, an example of apparatus 1 adapted to prepare a composition (in particular the composition according to the present invention) in submicrometric powder form starting from a liquid solution, or suspension (in particular aqueous), the apparatus 1 utilising the "Nano Spray" atomization technology and subsequent drying.

The apparatus 1 comprises a drying chamber 9 travelled by a flow of air (represented in FIG. 6A by arrows with solid lines) moved by means of an aspirator 90 and hence heated by a heater 91 (for example an electric resistor), the aspirator 90 and the heater 91 being both positioned preferably upstream of the drying chamber 9. In the initial portion of the drying chamber 9 is installed an atomization head 8, to which is associated a line for feeding the liquid solution, or suspension, said feeding line comprising a container 83, in which the liquid solution, or suspension, is loaded, and a suction pump 85, preferably a peristaltic pump, suitable to convey the liquid solution, or suspension, from the container 83 to the atomization head 8.

The atomization head 8 comprises a membrane (specifically made of stainless steel) that atomizes the liquid solution, or suspension, said membrane being provided with an array of holes of micrometric dimensions, the diameter of said holes being advantageously between 2.5 micrometres and 7 micrometres. To the membrane is then associated a piezoelectric crystal that serves as an actuator, inasmuch as, vibrating at an appropriate frequency (in particular at an ultrasonic frequency), causes the vibration of the membrane and hence the release of the liquid solution, or suspension, through the holes of the membrane.

The liquid solution, or suspension is then released in the drying chamber 9 in the form of drops, uniformly distributed and having controlled submicrometric dimensions. Once they are in the drying chamber 9, the drops are then driven by the flow of air, which also dries them. The trajectories travelled by the liquid solution, or suspension atomized and then dried in powder form are schematically illustrated in FIG. 6A by dashed lines.

The process used for preparing the composition in powder form is such as to charge electrically the submicrometric particles of the composition, which in particular acquire a negative electric charge.

The property of the particles of being electrically charged is advantageously exploited in the apparatus 1 to collect the powder. In particular, in the final portion of the drying chamber 9 is installed an electrostatic particle collector. Such collector comprises a negative electrode 77 connected to ground and a positive electrode 7 for collecting the particles, the positive electrode 7 preferably being applied to the lateral walls of the drying chamber 9 and surrounding the negative electrode 77. The particles of composition carried by the air flow, being negatively charged, are attracted by the positive electrode 7, where they are deposited, thereby separating from the air flow. The composition in powder form accumulated on the positive electrode 7 is then collected by means of an appropriate device (for example a spatula).

The air flow is advantageously evacuated from the drying chamber 9 after traversing a purifying device 88 (for example a HEPA filter) suitable to prevent any active molecules not deposited on the positive electrode 7 from being released into the environment. To control the temperature inside the drying chamber 9, a first probe 74 and a second probe 94 are installed respectively in the inlet section and in the outlet section of the drying chamber 9.

There are numerous control parameters which the apparatus 1 allows to regulate and that affect for example the size of the composition particles prepared by means of the apparatus 1, including in particular:

- the diameter of the holes of the membrane of the atomisation head 8;
- the vibration frequency of the piezoelectric crystal of the atomisation head 8;
- the capacity of the suction pump 85;
- the concentration of the active molecules in the liquid solution, or suspension;
- the capacity of the aspirator 90 and
- the temperature at the inlet of the drying chamber 9.

The apparatus 1 according to the "Nano Spray" technology shown in FIG. 6A has numerous, significant advantages. Since the particles are connected exploiting their electrical properties, it is possible to isolate particles of submicrometric dimensions. Moreover, the air flow in the drying chamber 9 can be substantially laminar with a relatively long time of permanence of the particles and a consequent effective drying thereof even at relatively low temperatures. Lastly, the apparatus 1 has a particularly high yield.

FIG. 6B shows, by way of non-limiting explanation, an example of apparatus 2 adapted to prepare a composition (in particular the composition according to the present invention) in micrometric powder form starting from a liquid solution, or suspension (in particular aqueous), the apparatus 2 utilising the "Mini Spray" atomization technology and subsequent drying.

The apparatus 2 comprises a drying chamber 49 travelled by a flow of air (represented in FIG. 6B by arrows with solid lines) moved by means of an aspirator 40 and hence heated by a heater 41 (for example an electric resistor), the aspirator 40 being positioned preferably upstream of the drying chamber 49, the aspirator 40 being positioned preferably downstream of the drying chamber 9. In the initial portion of the drying chamber 49 is installed a nozzle 48, to which is associated a line for feeding the liquid solution, or suspension, said feeding line comprising a container 38, in which the liquid solution, or suspension, is loaded, and a suction pump 58, preferably a peristaltic pump, suitable to convey the liquid solution, or suspension, from the container 38 to the nozzle 48.

To the nozzle 48 is further associated a pneumatic feeding line 23 travelled by a flow of pressurised gas, for example air or nitrogen. The pressurised air flow meets the liquid solution, or suspension, in the initial segment of the nozzle 48. In the body of the nozzle 48 the mixing of the liquid solution, or suspension, with the pressurised gas takes place and hence the pneumatic atomisation of the liquid solution, or suspension. In the final segment of the nozzle 48, distinguished by a converging direction, the liquid solution, or suspension, mixed to the pressurised gas, is further accelerated to then be released in the drying chamber 49 through the outlet section of the nozzle 48. The diameter of the outlet section of the nozzle 48 is preferably between 0.25 millimetres and 1 millimetre. The liquid solution, or suspension, is then released in the drying chamber 49 in the form of drops, uniformly distributed and having controlled micrometric dimensions. Once they are in the drying chamber 49, the drops are then driven by the flow of air, which also dries them. The trajectories travelled by the liquid solution, or suspension atomized and then dried in powder form are schematically illustrated in FIG. 6B by dashed lines.

The air flow is evacuated from the drying chamber 9 by means of an outlet section positioned in the final portion of the drying chamber 49, advantageously obtained in a lateral wall of the final portion of the drying chamber. On the bottom wall of the drying chamber 49 is instead obtained an exhaust opening, into which precipitate by gravity any residues (specifically, particles having greater dimensions than the desired dimensions) which are then collected in a container 35 to be then disposed of, after disconnecting the container 35 from the drying chamber 49. To control the temperature inside the drying chamber 49, a first probe 19 and a second probe 18 are installed respectively in the inlet section and in the outlet section of the drying chamber 9.

Downstream of the drying chamber 9 is then positioned a cyclone separator 3, configured to cause the loss of kinetic energy (and consequently of speed) from the air flow that carries the composition particles, which precipitate towards the bottom of the cyclone separator 3, in which is obtained an opening that communicates with a collecting casing 93. The composition in powder form then accumulates in the collecting casing 93, to be then withdrawn, after disconnecting the collection casing 93 from the cyclone separator 3. In the summit of the cyclone separator 3 is instead obtained an outlet section for the air flow. The air flow is then discharged from the cyclone separator 3 after traversing a purification device 12 (for example a HEPA filter) suitable to prevent any active molecules not precipitated in the collecting casing 93 (specifically because their dimensions are smaller than the desired dimension) can be released into the environment.

There are numerous control parameters which the apparatus 2 allows to regulate and that affect for example the size of the composition particles prepared by means of the apparatus 2, including in particular:
  the diameter of the outlet section of the nozzle 48;
  the capacity of the suction pump 85;
  the concentration of the active molecules in the liquid solution, or suspension;
  the flow rate of the pressurised gas in the pneumatic feed line 23;
  the capacity of the aspirator 40 and
  the temperature at the inlet of the drying chamber 49.

While the apparatus 2 according to the "Mini Spray" technology as shown in FIG. 6B has numerous and significant advantages (including a particularly high yield), nevertheless it allows to prepare particles with greater dimensions with respect to the particles that can instead be prepared by means of the apparatus 1 according to the "Nano Spray" technology shown in FIG. 6A. Micrometric dimensions of the particles are necessary for them to succeed, in the cyclone separator 3, in separating from the air flow that carries them and in precipitating by gravity into the collecting casing 93.

Preferably, the process according to the seventh object of the invention allows to obtain a composition in powder form having a particle diameter between 100 nm and 5 microns, preferably between 200 nm and 2.5 micron, still more preferably between 400 nm and 800 nm.

An eighth object of the invention is the process for preparing the composition in liquid solution, or suspension, form as defined in the second object of the invention comprising the following step:
  A) to a colloidal chitosan solution, adding an aqueous solution of alginic acid, or sodium alginate, and of pectin
  B) raising the pH of the resulting composition to a value between 4.5 and 6.5 pH units utilising a 0.1M NaOH solution in water
  C) optionally adding
    a solution of at least one further polysaccharide selected from dextran, α- and β-glycans, carrageenan, heparin, hyaluronic acid and sodium hyaluronate, preferably selected from hyaluronic acid and sodium hyaluronate
    and/or
    a solution of at least one ingredient selected from: soothing agents, cicatrizing agents, growth factors, peptides, anti-inflammatory agents and antimicrobials
    and/or
    at least one inorganic salt selected from: sodium carbonate and sodium or potassium bicarbonate, preferably sodium bicarbonate.

Preferably, the process according to the eighth object of the invention comprises the following step:
  A) to a colloidal chitosan and sodium tripolyphosphate solution, adding an aqueous solution of alginic acid, or sodium alginate, and of pectin
  B) raising the pH of the resulting composition to a value between 4.5 and 6.5 pH units utilising a 0.1M NaOH solution in water
  C) optionally adding
    a solution of at least one further polysaccharide selected from dextran, α- and β-glycans, carrageenan, heparin, hyaluronic acid and sodium hyaluronate, preferably selected from hyaluronic acid and sodium hyaluronate
    and/or
    a solution of at least one ingredient selected from: soothing agents, cicatrizing agents, growth factors, peptides, anti-inflammatory agents and antimicrobials.

Preferably, the process according to the eighth object of the invention further comprises the following steps:
  a) preparing an aqueous solution of alginic acid or sodium alginate,
  b) adding the pectin to the solution prepared in a);
  c) preparing an acidic aqueous or acidic hydroalcoholic, ethanol or isopropanol based, solution, of chitosan d) optionally adding an aqueous solution of sodium tripolyphosphate to the solution prepared in c) obtaining a solution of colloidal chitosan.

Preferably in the process according to the eighth object of the invention the total concentration of the polysaccharides of the composition in liquid solution, or suspension, form defined in the second object of the invention is at least 0.25% w/v, preferably at least 0.40% w/v; preferably, it is between 0.25% and 5.0% w/v, more preferably it is between 0.40% and 1.5% w/v.

Preferably in the process according to the eighth object of the invention the alginic acid or the sodium alginate has a high content of mannuronic acid residues; the pectin is amidated and it has a low degree of methoxylation (DM); the chitosan has low molecular weight, as described according to the second object of the invention.

In an embodiment of the process according to the eighth object of the invention that utilises a hydroalcoholic solution, said solution is from 2.5% to 25% volume/volume; more preferably 5% volume/volume.

In an embodiment of the process according to the eighth object of the invention that utilises a hydroalcoholic solution, the process also comprises the step of eliminating the hydroalcoholic solvent/dispersing agent by evaporation at lower temperatures than the evaporation temperature of water alone.

Soothing agents, cicatrizing agents, growth factors, peptides, anti-inflammatory agents, antimicrobials and inorganic salts suited for the process according to the eighth object of the invention are the same listed with regard to the first and second object of the invention.

A ninth object of the invention is the use of the composition in powder form as defined in the first object of the invention, in the field of food and in particular for the preservation of foods.

Preferably, according to the ninth object of the invention the weight ratio between the food and the powder as defined in the first object of the invention is between 100:1 and 500:1; more preferably, it is between 200:1 and 300:1.

As will be discussed in greater depth in the experimental part, the powder of the invention is able to control the microbial development even without adding active ingredients having antimicrobial activity. Indeed, the powder of the invention is able to adsorb liquids and humidity that are formed in fresh foods during their preservation, thus allowing to prolong the quality, safety and sensorial properties of the food to be preserved and serving as active packaging for fresh food products.

Experimental Part

Example 1—Preparation of the Liquid Compositions 1A) aqueous composition (without inorganic salts)
1a) Preparation of the sodium alginate solution
53.6 mg of sodium alginate (FMC Biopolymer) having content of mannuronic residues of 65% by weight with respect to the total weight of the sodium alginate, were added to 21.4 ml of distilled water leaving the solution under agitation for approximately 10 minutes.

1b) Preparation of the sodium alginate and pectin aqueous composition
To the sodium alginate solution prepared as described in a) were added 53.6 mg of amidated pectin (Herbstreith & Fox) having a degree of amidation (DA) between 18-23% and a degree of methoxylation (DM) between 27-32%, leaving the resulting solution under agitation for 15 minutes.

1c) Preparation of the colloidal chitosan solution
8.9 mg of chitosan (Sigma Aldrich) having molecular weight between 50000 and 150000 DA were added to 3.6 ml of a solution of HCl 0.1 M in distilled water leaving under agitation for approximately 15 minutes; to the resulting acidic chitosan solution were added 1.45 ml of an aqueous solution of sodium tripolyphosphate 10 mM.

1d) Preparation of the sodium alginate, pectin and chitosan aqueous composition (INVENTION)
The colloidal chitosan and sodium tripolyphosphate solution prepared as described in 1c) was added slowly and under continuous agitation to the solution of alginate and pectin prepared as described in 1b); the pH of the resulting composition was raised to the value of 5.3 utilising a NaOH 0.1M solution in water.

1e) Preparation of the sodium alginate, pectin and chitosan+doxycycline aqueous composition (INVENTION)
An aqueous doxycycline solution was prepared adding 1.1 mg of doxycycline hyclate (Sigma-Aldrich) to 1 ml of deionized water. The solution thus obtained was added slowly to the aqueous composition of the invention (1d) and left under continuous agitation for 10 minutes.

1B) hydroalcoholic composition (without inorganic salts)
1c') Preparation of the hydroalcoholic—$H_2O$/Ethanol colloidal chitosan solution
96.2 mg of chitosan (Sigma Aldrich) having molecular weight between 50000 and 150000 DA were added to 70 ml of a solution of $CH_3COOH$ 1% weight/volume in distilled water leaving under agitation for approximately 15 minutes; to the resulting acidic chitosan solution were added 10 ml of a solution of $H_2O$/Ethanol (96°) 50:50 volume/volume under agitation.

1d') Preparation of the hydroalcoholic composition—$H_2O$/Ethanol of sodium alginate, pectin and chitosan (INVENTION)
The colloidal hydroalcoholic chitosan solution prepared as described in 1c') was added slowly and under continuous agitation to the solution of alginate and pectin prepared as described in 1b); the pH of the resulting composition was raised to the value of 5.3 utilising a NaOH 0.1M solution in water.

1C) Aqueous composition comprising an inorganic salt according to the invention
1c") Preparation of the aqueous colloidal chitosan solution
96.2 mg of chitosan (Sigma Aldrich) having molecular weight between 50000 and 150000 DA were added to 70 ml of a solution of $CH_3COOH$ 1% weight/water in distilled water leaving under agitation for approximately 15 minutes.

1d") Preparation of the sodium alginate, pectin and chitosan and sodium bicarbonate aqueous composition (INVENTION)
The aqueous colloidal chitosan solution prepared as described in 1c") was added slowly and under continuous agitation to the solution of alginate and pectin prepared as described in 1b); to the resulting solutions were added 12.4 mg of sodium bicarbonate corresponding to 6.1% weight/weight with respect to the total weight of the polymers.

1D) Aqueous composition comprising an inorganic salt (COMPARISON)
1d") Preparation of the sodium alginate, pectin and chitosan and ammonium carbonate aqueous composition
The aqueous colloidal chitosan solution prepared as described in 1c") was added slowly and under continuous agitation to the solution of alginate and pectin prepared as described in 1b); to the resulting solutions were added 10.17 mg of ammonium carbonate corresponding to 5% weight/weight with respect to the total weight of the polymers.

Example 2—Preparation of the Composition in Powder Form 2A) preparation of the composition in submicrometric powder form
A sample of each of the liquid compositions obtained respectively in the examples 1b (COMPARISON), 1d and 1e (INVENTION) was maintained under continuous agitation and was subjected to an atomization process by nanospray drying technology by means of Nano Spray Dryer B-90 apparatus (Buchi Laboratoriums-Tecnik, Flawil, Switzerland).

The inlet Temperature in the atomizer of the composition 1b (COMPARISON) was 90° C., while the inlet Temperature of the specific composition 1d or 1e (INVENTION) was 50° C., i.e. advantageously lower.

The remaining process parameters were the same both for the comparison composition, and for the composition of the invention, as described below:
Atomizer feeding rate 9.5 ml/min;
Diameter of the atomizing nozzle 4.0 micron;
Incoming air flow rate 100 L/min;
Pressure in drying chamber 38 mbar;
Relative spray rate 90%

Such parameters allowed to obtain from the respective liquid compositions a powder whose particles have submicrometric dimensions with an average yield of the process above 85% expressed as average percentage of final product compared with the quantity of material processed.

Specifically, from the aqueous composition 1b (COMPARISON) was obtained the composition in submicrometric powder form 2b1 (COMPARISON)

from the aqueous composition 1d (INVENTION) was obtained the composition in submicrometric powder form 2d1 (INVENTION)

from the aqueous composition 1e (INVENTION) was obtained the composition in submicrometric powder form 2e1 (INVENTION)

2A') preparation of the composition in submicrometric powder form

A sample of each of the liquid compositions obtained respectively in the examples 1d' and 1d'' (INVENTION) and 1d''' (COMPARISON) was maintained under continuous agitation and was subjected to an atomization process by nanospray drying technology by means of Nano Spray Dryer B-90 apparatus (Buchi Laboratoriums-Tecnik, Flawil, Switzerland). The inlet Temperature in the atomizer of the compositions 1d', 1d'' and 1d''' was 50° C.

The remaining process parameters were the same both for the comparison composition, and for the composition of the invention, as described below:

Atomizer feeding rate 9.5 ml/min;
Diameter of the atomizing nozzle 4.0 micron;
Incoming air flow rate 100 L/min;
Pressure in drying chamber 38 mbar;
Relative spray rate 90%

Such parameters allowed to obtain from the respective liquid compositions a powder whose particles have submicrometric dimensions with an average yield of the process above 85% expressed as average percentage of final product compared with the quantity of material processed.

Specifically, from the hydroalcoholic composition—H$_2$O/Ethanol 1d' (INVENTION) was obtained the composition in submicrometric powder form 2d'1 (INVENTION)

from the aqueous composition comprising sodium bicarbonate 1d'' (INVENTION) was obtained the composition in submicrometric powder form 2d''1 (INVENTION)

from the aqueous composition comprising ammonium carbonate 1d''' (COMPARISON) was obtained the composition in submicrometric powder form 2d'''1 (COMPARISON).

2B) preparation of the composition in micrometric powder form

Another sample of each of the liquid compositions obtained respectively in the examples 1b (COMPARISON), 1d and 1e (INVENTION) was maintained under continuous agitation and was subjected to an atomization process by minispray drying technology by means of Mini Spray Dryer B-191 apparatus (Buchi Laboratoriums-Tecnik, Flawil, Switzerland).

In the case of the Mini Spray Drying process, too, the inlet temperature in the atomizer of the composition 1d or 1e (INVENTION) was lower, i.e. 105° C., than the temperature necessary to process the composition 1b (COMPARISON) which was 120° C.

Specifically, from the aqueous composition 1b (COMPARISON) was obtained the composition in micrometric powder form 2b2 (COMPARISON) and from the aqueous composition 1d (INVENTION) was obtained the composition in micrometric powder form 2d2 (INVENTION)

from the aqueous composition 1e (INVENTION) was obtained the composition in micrometric powder form 2e2 (INVENTION).

Example 3—Morphological Analysis of the Composition in Powder Form of the Invention The compositions in powder form according to the invention (2d1) and (2d2) prepared respectively by nanospray and minispray drying technology as described in the example 2A or 2B were analysed by Scanning Electron Microscopy (SEM) by means of a Carl Zeiss EVO MA 10 microscope equipped with a secondary electron detector (Carl Zeiss SMT Ltd, Cambridge, UK). The powder particles were coated by a 200 Å thick gold patina by means of a LEICA EMSCD005 metallizer. The analyses were conducted at 20 KeV. A minimum of 20 SEM images were obtained for each individual sample, to verify the morphological uniformity of the particles.

Figure 1A:
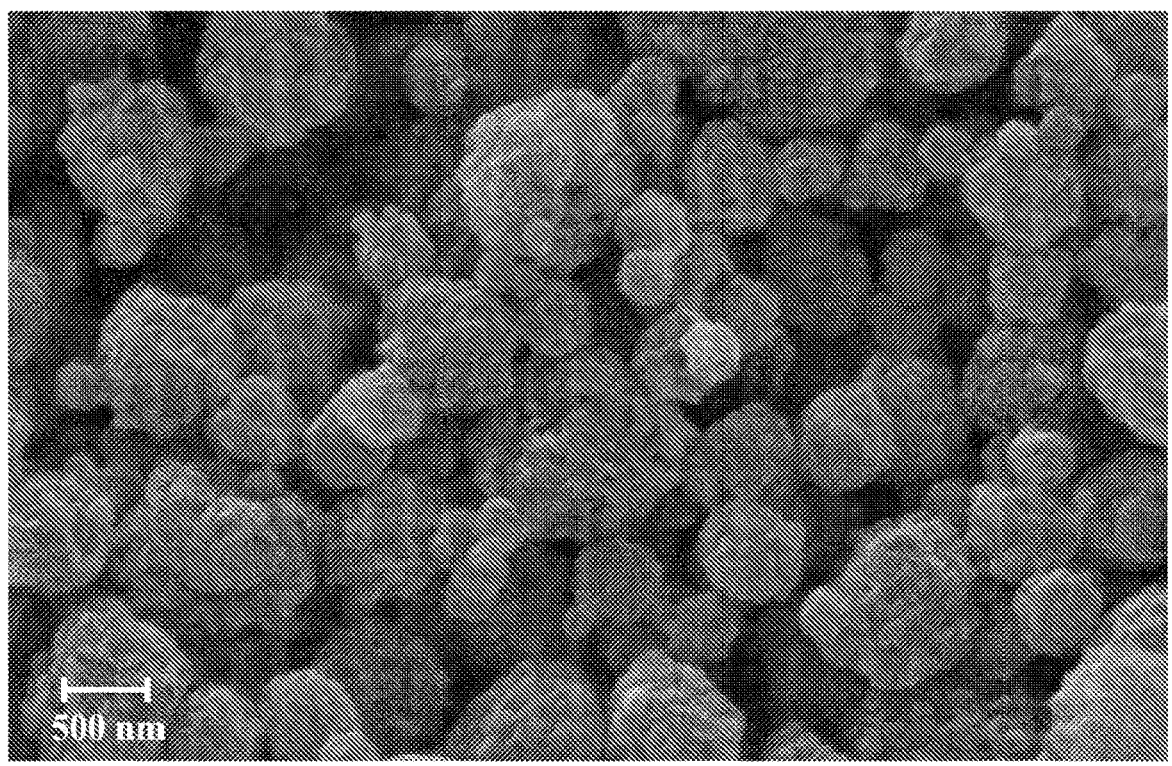
FIG. 1A shows an image obtained by SEM of a representative sample of the particles of submicrometric powder according to the invention (2d1) prepared as described in example 2A.

As shown in FIG. 1A, from the SEM analysis it was found that the particles of submicrometric powder (2d1) have spherical shape and high surface roughness, which makes the particles susceptible to contact with the fluid.

Figure 1B:
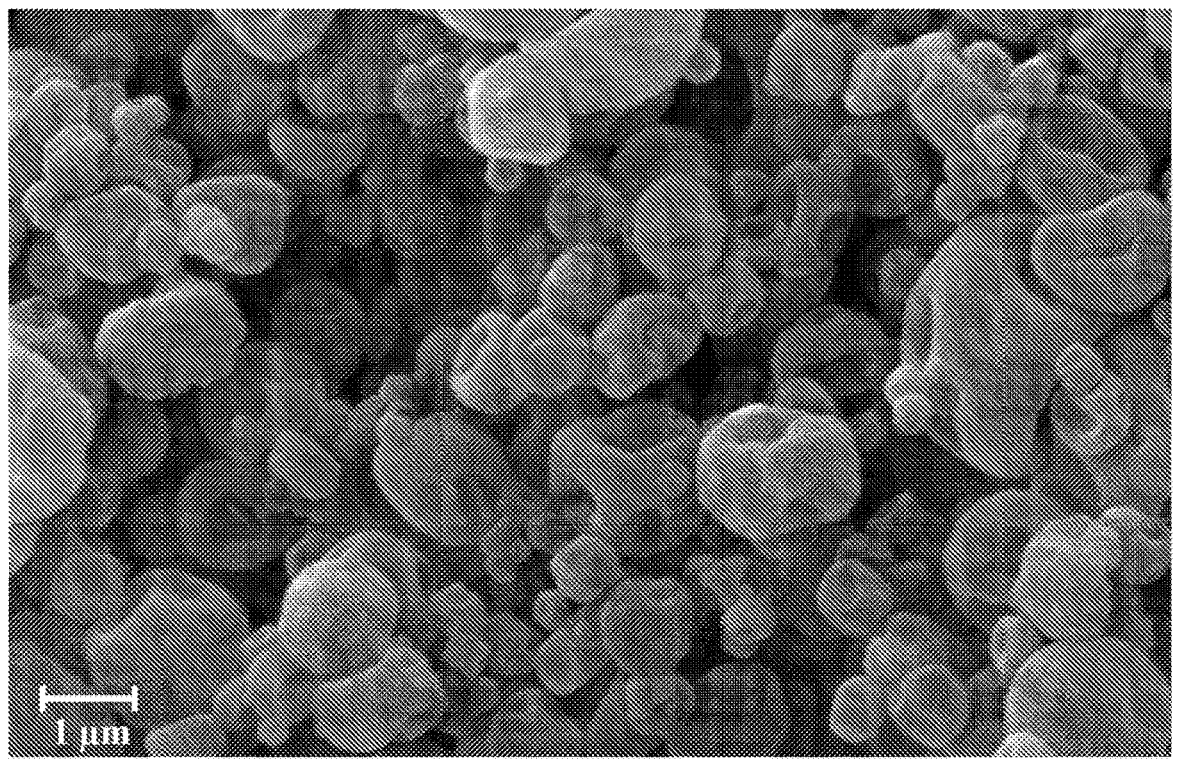
FIG. 1B shows an image obtained by SEM of a representative sample of the particles of micrometric powder according to the invention (2d2) prepared as described in example 2B.
Figure 1C:
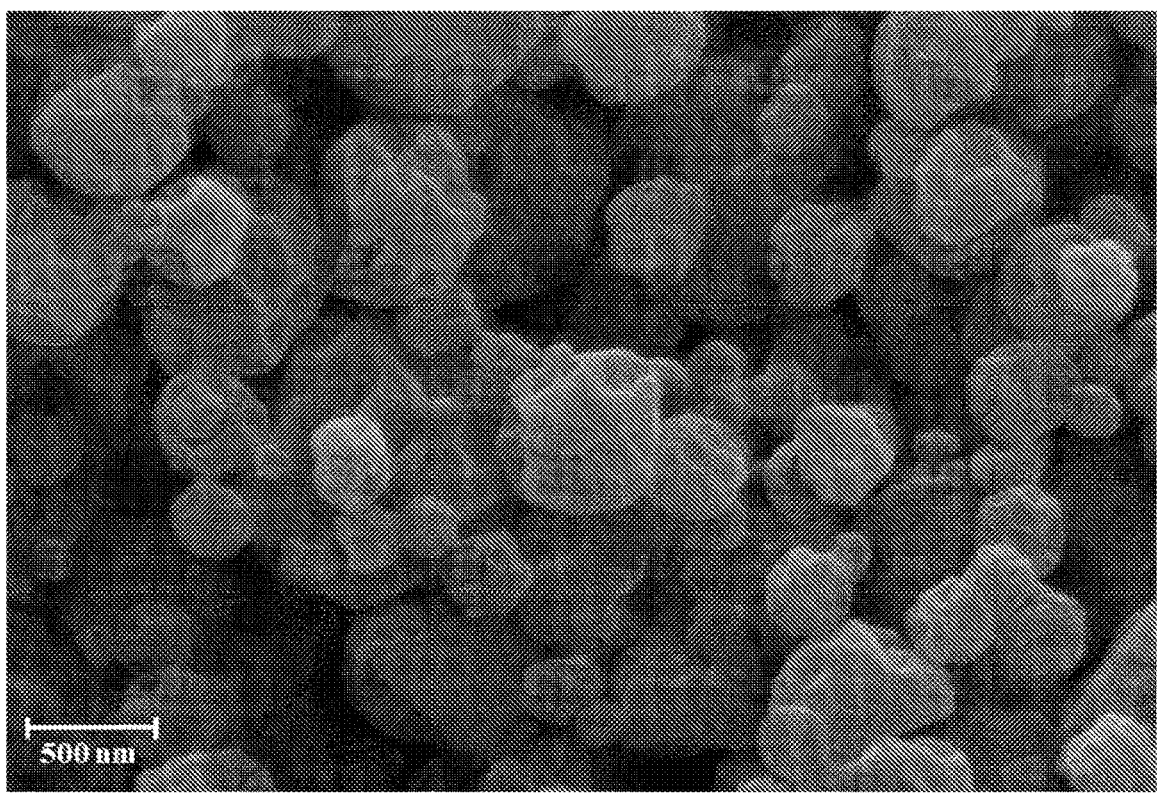
FIG. 1C shows an image obtained by SEM of a representative sample of the particles of submicrometric powder according to the invention (2d'1) prepared as described in example 2A'.

As shown in FIG. 1B, from the SEM analysis it was found that the particles of micrometric powder (2d2) have prevalently spherical shape and lower surface roughness than the roughness of the submicrometric powder (2d1).

The compositions in powder form according to the invention (2d'1) and (2d''1) and the comparison composition in powder form (2d'''1) prepared by nanospray drying technology as described in the example 2A' were also analysed by Scanning Electron Microscopy (SEM) as described above.

As shown in FIG. 10, from the SEM analysis it was found that also the particles of submicrometric powder (2d'1) obtained from hydroalcoholic—H$_2$O/Ethanol composition have spherical shape and high surface roughness, which makes the particles susceptible to contact with the fluid.

Figure 1D:
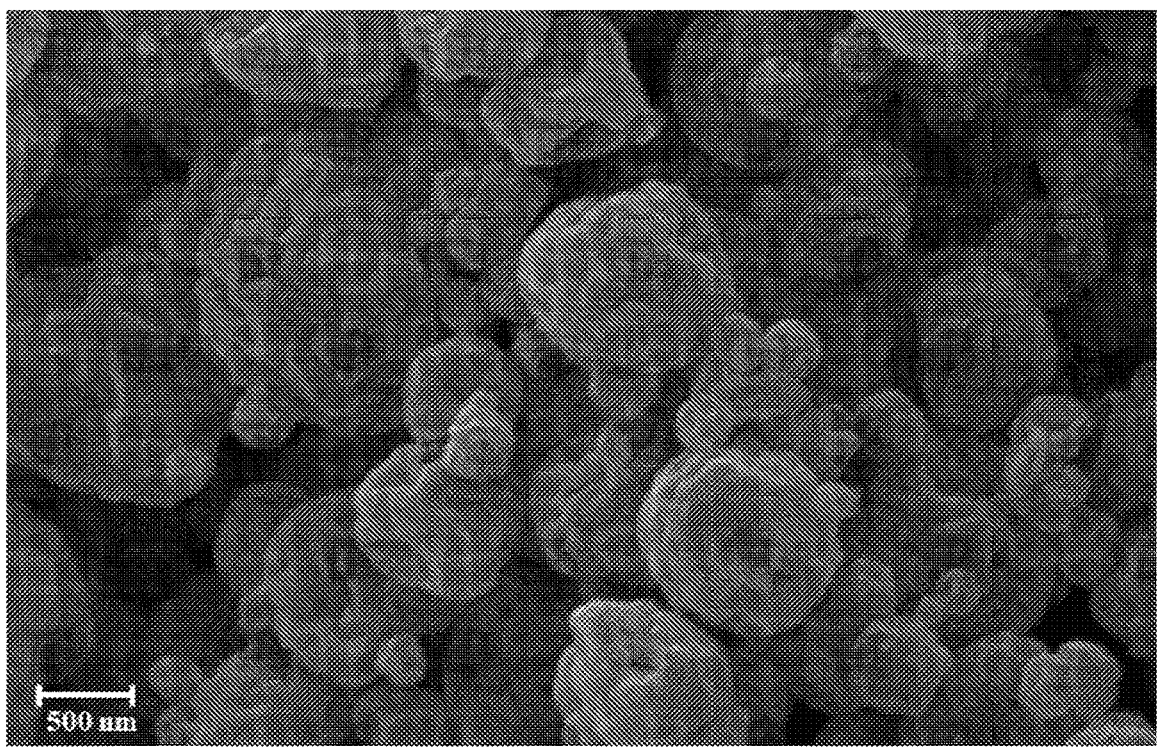
FIG. 1D shows an image obtained by SEM of a representative sample of the particles of submicrometric powder according to the invention (2d"1) prepared as described in example 2A'.

As shown in FIG. 1D, from the SEM analysis it was found that also the particles of submicrometric powder (2d''1) obtained from aqueous compositions comprising sodium bicarbonate have spherical shape and high surface roughness, which makes the particles susceptible to contact with the fluid.

Figure 1E:
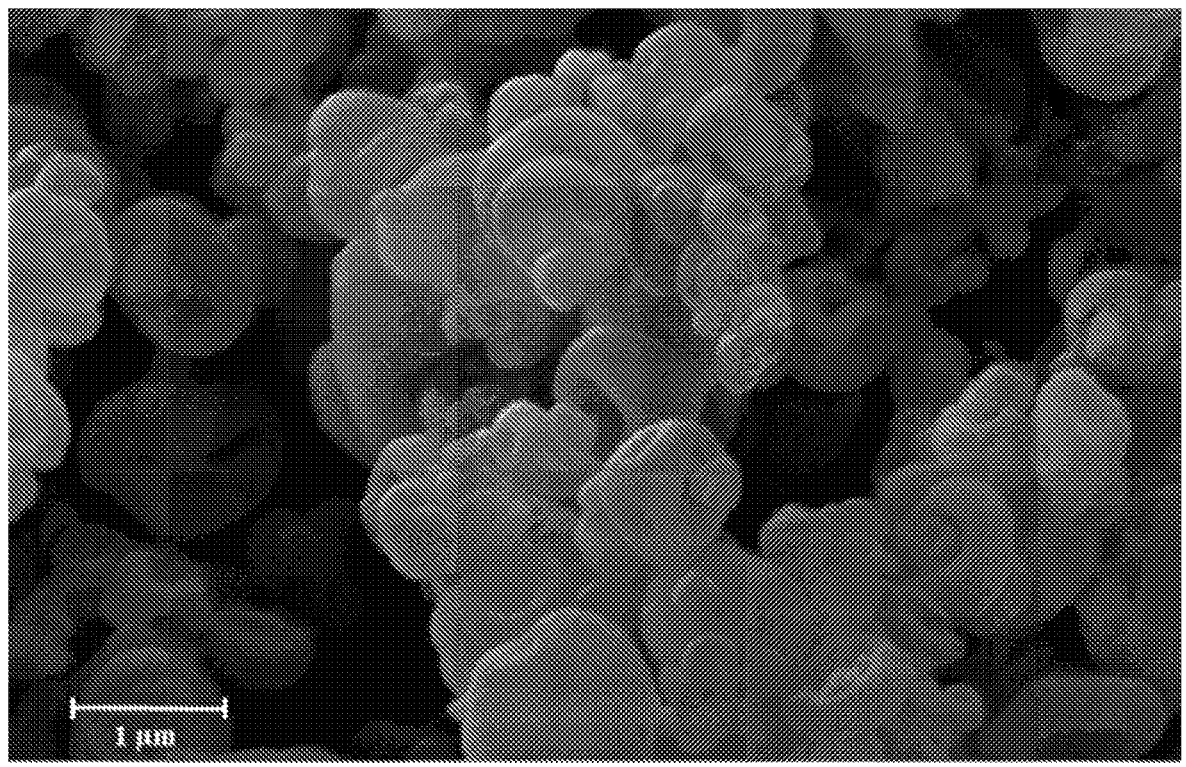
FIG. 1E shows an image obtained by SEM of a representative sample of the comparison particles of submicrometric powder (2d'''1) prepared as described in example 2A'.

As shown in FIG. 1E, from the SEM analysis it was found that the comparison particles of submicrometric powder (2d'''1) obtained from aqueous compositions comprising ammonium carbonate have ellipsoidal shape with little surface roughness, which makes the particles less susceptible to contact with the fluid.

Example 4—Dimensional Analysis of the Composition in Powder Form of the Invention The dimensional distribution of the composition in submicrometric powder form according to the invention (2d1) prepared as described in the example 2A with Nano Spray Dryer technology was evaluated with the Dynamic Light Scattering (DLS) technique by means of an N5 apparatus (Beckman Coulter, Miami, Fla.). Each sample was dispersed in dichloromethane, sonicated for 2 minutes and analysed with a 90° detector. For each sample the average diameter and the dimensional distribution was obtained as the mean of the results obtained analysing 3 samples of the same production lot and analysing a minimum of 3 lots. To verify the capability of the sonication process to bring the particles in dispersion, analyses were conducted with different sonication times, ranging from 2 to 30 minutes, without recording any significant variation of the data thus obtained.

As shown in FIG. 2A, from the DLS analysis it was found that the particles of powder (2d1) have a mean diameter of approximately 0.50 micron (500 nm).

The dimensional distribution of the composition in micrometric powder form according to the invention (2d2) prepared as described in the example 2B with minispray technology was evaluated with the Light Scattering (LS) technique by means of an LS13320 apparatus (Beckman Coulter, Miami, Fla.). Each sample was dispersed in dichloromethane, sonicated for 2 minutes and analysed with a 90° detector. For each sample the average diameter and the dimensional distribution was obtained as the mean of the results obtained analysing 3 samples of the same production lot and analysing a minimum of 3 lots.

As shown in FIG. 2B, from the LS analysis it was found that the particles of this powder have a mean diameter of approximately 4.25 micron.

The dimensional distribution of the comparison composition in submicrometric powder form (2b1) prepared as described in the example 2A with Nano Spray Dryer technology was evaluated with the Dynamic Light Scattering (DLS) technique by means of an N5 apparatus (Beckman Coulter, Miami, Fla.). Each sample was dispersed in dichloromethane, sonicated for 2 minutes and analysed with a 90° detector. For each sample the average diameter and the dimensional distribution was obtained as the mean of the results obtained analysing 3 samples of the same production lot and analysing a minimum of 3 lots. To verify the capability of the sonication process to bring the particles in dispersion, analyses were conducted with different sonication times, ranging from 2 to 30 minutes, without recording any significant variation of the data thus obtained.

As shown in FIG. 2C, from the DLS analysis it was found that the particles of this powder (2b1) have a mean diameter of approximately 0.76 micron.

After 30 days of preservation in conditions of accelerated stability, an evaluation was also made of the dimensional distribution of the particles of the same sample of submicrometric powder according to the invention (2d1) and of the particles of submicrometric powder (2b1) (COMPARISON) used above.

The experiments of accelerated stability of the powders were conducted following the ICH Q1AR2 guidelines "Stability testing of New Drug Substances and Products", preserving the powders in amber glass at 40° C. and 75% of relative humidity for a period of 30 days. At the end of this period, the samples were analysed with SEM and DLS techniques as described above.

It was shown that both the particles of powder (2d1) and those of powder (2b1) maintain their morphological characteristics after 30 days of preservation in conditions of accelerated stability.

As shown in FIG. 2A', the particles of powder (2d1) after 30 days of preservation in conditions of accelerated stability maintain a nearly unchanged dimensional distribution, with a variation of approximately 5% with respect to the dimensional distribution shown in FIG. 2A.

On the contrary, as shown in FIG. 2C' the particles of powder (2b1) consisting only of alginate and pectin after 30 days of preservation in condition of accelerated stability undergo a considerable expansion of the dimensional distribution, with 20% variation with respect to the dimensional distribution at time zero, shown in FIG. 2C.

The compositions in powder form according to the invention (2d'1) and (2d"1) and the comparison composition in powder form (2d'''1) prepared by nanospray drying technology as described in the example 2A' were also analysed by Scanning Electron Microscopy (SEM) as described above.

As shown in FIG. 2D, from the DLS analysis it was found that the particles of powder (2d'1) obtained from hydroalcoholic—$H_2O$/Ethanol composition have a mean diameter smaller than 0.50 micron (smaller than 500 nm) and a narrow dimensional distribution.

As shown in FIG. 2E, from the DLS analysis it was found that the particles of powder (2d"1) obtained from aqueous compositions comprising sodium bicarbonate have a mean diameter of approximately 0.70 micron (700 nm) and a narrow dimensional distribution.

As shown in FIG. 2F, from the DLS analysis it was found that the particles of powder (2d'''1) obtained from aqueous compositions comprising ammonium carbonate have a mean diameter of approximately 1 micron.

Example 5—Gelification Time and Capacity to Absorb Exudate by the Composition in Powder Form of the Invention The capacity to absorb exudate over time by each of the compositions in powder form according to the invention (2d1) and (2d2) was evaluated calculating the ratio between the fluid content at equilibrium after gelification and the weight of the dry powder.

Specifically, 15 mg of powder prepared as described in the example 2A was placed on a disk of previously weighed filter paper. The disk was placed in contact with a donor compartment containing simulated wound fluid (SWF), whose composition is 50% fetal calf serum (Sigma-Aldrich, Milan, Italy), 50% maximum recovery diluent (Sigma-Aldrich, Milan, Italy, consisting of 0.1% (w/v) peptone and 0.9% (w/v) sodium chloride) thermostated at 37° C.

The weight of the gel being formed was recorded with precision scale at precise time intervals. All experiments were conducted on a minimum number of 6 samples per individual lot produced and the results expressed as mean±standard deviation. The difference between the weight of the gel formed at equilibrium and the weight of the dry powder represents the weight of the fluid absorbed at equilibrium, which was related to the weight of the dry powder.

FIG. 3A shows the complete gelification of the submicrometric powder of the invention (2d1).

The charts of FIG. 3B show that the complete gelification of the submicrometric powder (2d1) and of the micrometric powder (2d2) takes place respectively in approximately 3-5 minutes and 5-10 minutes.

These results are particularly advantageous, as 15 mg of alginate/pectin composition in submicrometric powder form described in De Cicco et al, (2014) International Journal of Pharmaceutics 473: 30-37 require a longer time for complete gelification, i.e. 10-15 minutes; also, 15 mg of alginate/pectin micrometric powder described in De Cicco F et al, (2014), Carbohydrate Polymers 101:1216-122 require a longer time for complete gelification, i.e. approximately 30 minutes.

Moreover, the charts of FIG. 3B show that the capacity to absorb exudate by the powder according to the invention is very high; in particular, the submicrometric powder (2d1) has a capacity to absorb exudate comprised between 10 and 15 times its dry weight.

Similarly to the above description, an evaluation was made of the gelification rate of 15 mg of submicrometric powder (2d1) prepared in the example 2A compared with 15 mg of alginate only, 15 mg of pectin only, and 15 mg of chitosan only, which were obtained with the same process and applying the same operating conditions described in example 2A.

In FIG. 3C, the chart pertaining to the submicrometric powder (2d1) confirms that the complete gelification of 15 mg of this powder takes place in approximately 3-5 minutes.

FIG. 3C moreover shows that the % increase of the weight of the dry powder following gelification ($\Delta$) of the submicrometric powder (2d1) within 5 minutes from contact between the powder and the simulated wound fluid, is approximately 1619, i.e. approximately 3 times greater than that of the powder based on alginate only ($\Delta$ approximately 540) and that of the powder based on pectin only ($\Delta$ approximately 560) and more than 3 times greater than that of the powder based on chitosan only ($\Delta$ approximately 515).

As described in De Cicco et al, (2014), International Journal of Pharmaceutics 473: 30-37, within 5 minutes from contact between 15 mg of powder and the simulated wound fluid, the $\Delta$ of the alginate/pectin submicrometric powder is between 500 and 624, therefore the A of the submicrometric powder (2d1) is between 3.2 and 2.5 times greater than the $\Delta$ of the powder described in that publication.

Moreover, the charts of FIG. 3C show that the gel formed from the powder according to the invention shows a constant volume once the maximum fluid absorption is reached, while the gels formed from powders based on pectin only or on chitosan only show over time a reduction in the quantity of fluid absorbed and the powder based on alginate only needs over 30 minutes to reach the maximum fluid absorption.

Similarly, an evaluation was also made of the capacity to absorb exudate over time by each of the compositions in powder form according to the invention (2d'1) and (2d"1) and comparison (2d'"1).

The complete gelification of the submicrometric powder (2d'1) obtained from hydroethanolic composition and of the submicrometric powder (2d"2) obtained from aqueous composition comprising sodium bicarbonate takes place respectively in approximately 50 seconds and in 20 seconds.

These results are particularly advantageous, inasmuch as they demonstrate that the gelification rate of powders obtained from specific hydroalcoholic compositions or from compositions comprising specific inorganic salts is also better than the gelification rate of the submicrometric powder (2d1), obtained from aqueous composition without addition of inorganic salts.

Without wishing to be bound to any particular theory, the present inventors deem that in the case of the particles of powder (2d'1) the elimination of the hydroalcoholic solvent determines a smaller mean diameter and a rougher surface of the particles with respect to the particles (2d1), such morphological parameters determine a decrease in the density of the powder, which then gelifies at a higher rate than the powder (2d1).

In the case of the particles of powder (2d"1), the elimination of the aqueous solvent containing the inorganic salt generates effervescence following the release of gaseous $CO_2$, which in turn determines a decrease in the density of the powder and a higher gelification rate thereof with respect to the powder (2d1).

The use of hydroalcoholic solutions that utilise a different alcohol from the one selected in the present invention, for example propanol or butanol, from 2.5% to 25% volume/volume, determined a worsening in the gelification time compared with the gelification time of the submicrometric powder (2d1).

The use of a inorganic salt different from those selected in the present invention, for example ammonium carbonate, determined a gelification time of 4 minutes, which is not improved with respect to the gelification time of the submicrometric powder (2d1) obtained from aqueous composition without addition of the inorganic salt.

Example 6—Evaluation of the Adhesive Capacity of the Gel Formed Following the In Situ Gelification of the Composition in Powder Form of the Invention The adhesive property of the gel formed in situ was evaluated by means of a tensile stress test, utilising an Electroforce 3200 tensile stress tester (Bose, Eden Prairie, Minn.) and applying a modified protocol with respect to the ASTM D3808 standard.

Specifically, approximately 15 mg of submicrometric powder (2d1) prepared as described in the example 2A was placed in contact with a nitrocellulose membrane, having pore dimension 0.45 µm and surface area of 3.14 $cm^2$, previously wet with SWF. After the formation of the gel, the membrane was placed on the sample holder of the tensile stress tester. The movement of the sample holder was set to 1 mm/min producing a compression of the gel against the loading head of the apparatus. The force necessary to detach the gel from the membrane on which it was formed was calculated by computing the force-time curve acquired by the instrument during the movement of the sample. All experiments were conducted on a minimum number of 6 samples per individual lot produced and the results expressed as mean±standard deviation.

The adhesive capacity of said gel formed in situ was found to be 11.6 kPa with an increase of approximately 22% on the better result described in the paper by De Cicco et al, (2014), International Journal of Pharmaceutics 473: 30-37 referred to the gel formed in situ from an alginate/pectin composition in powder form.

This result is particularly advantageous because it allows to avoid the risk of accidental detachment of the gel formed in situ while allowing an easy removal of the gel from the wound after use.

Example 7—Evaluation of the Water Vapour Transmission Rate (WVTR) of the Gel Formed Following the In Situ Gelification of the Composition in Powder Form of the Invention The WVTR was evaluated as described in the standard protocol ASTM, 2010.

Specifically, approximately 25 mm of a disk of gel formed in situ from the submicrometric powder (2d1) as described in the example 5 were placed on a plastic tube containing 20 ml of distilled water. A Teflon strip was used to cover the edge of the disk to avoid leaks from the edge. The system was maintained in an incubator at 37° C. The weight loss was recorded with precision scale at precise time intervals and tracked versus time. All experiments were conducted on a minimum number of 6 samples per individual lot produced and the results expressed as mean±standard deviation.

WVTR was calculated applying the following formula:

$$WVTR = slope/A$$

where

Slope is the slope of the track

A is the surface area of the tested sample in m².

The WVTR of this gel formed in situ was found to be within the range between 90 and 95 g/m²/h, which falls within the recommended range (80-105 g/m²/h); from this result, it is inferred that the gel is able to maintain a balanced hydration of the wound, preventing the exudate from determining occlusive phenomena or the occurrence of an excessive hydration of the wound.

Example 8—Comparative In Vitro Study of the Healing Capacity of Wounds by Evaluation of Cell Migration The induction of cell migration by the new composition in submicrometric powder form (2d1) prepared as described in the example 2A, was evaluated on the HaCaT cell line (immortalized human keratinocytes acquired from CLS Cell Lines Service GmbH (Germany). The cell maintenance medium used was Dulbecco's modified Eagle's medium (DMEM) with 10% of fetal bovine serum (FBS) with the addition of antibiotics (10000 U/ml penicillin and 10 mg/ml streptomycin). The cells were plated on 12-well plates utilising $5 \times 10^5$ and $10 \times 10^5$ cells for each well. The plates seeded as described above were divided in six groups:

- a first group of 3 plates was placed in contact with culture medium only (COMPARISON);
- each plate of a second group of 3 plates was placed in contact with 5.01 mg of alginate only (raw material, COMPARISON);
- each plate of a third group of 3 plates was placed in contact with 5.00 mg of pectin only (raw material, COMPARISON);
- each plate of a fourth group of 3 plates was placed in contact with 5.00 mg of chitosan only (raw material, COMPARISON);
- each plate of a fifth group of 3 plates was placed in contact with 5.01 mg of composition in submicrometric powder form (2b1) (alginate/pectin, COMPARISON);
- each plate of a sixth group of 3 plates was placed in contact with 4.99 mg of composition in submicrometric powder form (2d1) (alginate/pectin/chitosan, INVENTION).

After 24 hours of incubation, having reached 100% of confluence a groove was made at the centre of the cell monolayer by means of a sterile pipette tip. All experimental points provided treatment with minomycin C (10 µg/ml, Sigma Aldrich) to block cell mitosis. Cell monolayer having the cut were incubated at 37° C. in 5% $CO_2$ and 95% humidified area inside the incubation chamber of a Leica AF-6000 LX Integrated Live Cell Workstation.

The images of the cells during the experiment were acquired with the microscope by means of a 10× contrast lens used to record cell movements at an acquisition frequency of 10 minutes. The cell migration rate of the individual cells was determined by measuring the closure of the cut. For each individual cut, 10 different experimental points were recorded and for each experimental point 10 different cells were selected, at random, to measure the migration distance.

FIG. 4A shows an image representative of each group of cells: untreated (CTRL), alginate only (Alg), pectin only (Pect), chitosan only (Chit), composition in submicrometric powder form (2b1) (Alg/Pect), composition in submicrometric powder form (2d1) (Alg/Pect/Chit) acquired during the experiment at time 0 and 24 hours after the creation of the lesion of the cell monolayer.

From the images of FIG. 4A it is possible to note that the gel formed as a result of the in situ gelification of the composition in powder form according to the invention (2d1) has a greater capability to stimulate cell migration and accelerate the closure of the wound both compared with the gels formed as a result of the gelification of the individual pure polymers, and compared with the gels formed as a result of the gelification of the comparison powder composition (2b1).

FIG. 4B shows the cell migration rate, expressed as distance (µm) travelled in 24 h, of each group of cells: untreated (CTRL), alginate only (Alg), pectin only (Pect), chitosan only (Chit), composition in submicrometric powder form (2b1) (Alg/Pect), composition in submicrometric powder form (2d1) (Alg/Pect/Chit). Each figure is representative of three different experiments and is expressed as mean±standard deviation. The statistical comparisons between the groups were evaluated by t-test. A value of $P<0.05$ was considered to indicate a statistically significant difference.

The bar chart of FIG. 4B shows that the pro-migratory capacity of the submicrometric powder (2d1) (INVENTION) consisting of sodium alginate/pectin/chitosan is significantly greater than the pro-migratory capacity of the comparison submicrometric powder (2b1) consisting of sodium alginate/pectin.

Example 9—In Vitro Study of the Release of an Active Principle

In this experiment, the release of Doxycycline from the composition in submicrometric powder form (2e1) prepared as described in the example 2A in which the weight ratio Alg/Pect/Chit is 6/6/1 and from compositions in submicrometric powder form that differ from the previous one only in the weight ratio Alg/Pect/Chit which is respectively 3/1/1 and 1/1/1. A powder consisting of only doxycycline hyclate (raw material) was used as comparison.

The release of Doxycycline was monitored utilising vertical diffusion cells of the Franz type with SWF in the donor compartment. All experiments were conducted on a minimum number of 6 samples per individual lot produced and the results expressed as mean±standard deviation.

FIG. 5 shows the permeation curves of the compositions in submicrometric powder form according to the invention, in which the Alg/Pect/Chit weight ratio is respectively 6/6/1, 3/1/1 and 1/1/1, and the permeation curve of the powder of Doxycycline (Dox) alone.

The charts of FIG. 5 demonstrate that the composition of the invention can advantageously encapsulate an antimicrobial agent; moreover, these charts demonstrate that the rate of release of the antimicrobial agent can be controlled because of the different weight ratio of the polysaccharides that constitute the particles of the powder.

When present in the composition, the antimicrobial agent contributes to the complete eradication of the infection of the wound; by appropriately modulating the properties of the gel formed in situ, a quantity of active ingredient can be released immediately after the application and the remaining part with a release protracted in time.

Example 10—Study of the Capacity to Inhibit Microbial Growth on Foods

The capacity to inhibit microbial growth on foods by the new composition in submicrometric powder form (2d1)

prepared as described in the example 2A was evaluated utilising portions of poultry and beef preserved in standard conditions (4° C., 75% humidity) for 8 days.

From 5 to 12 mg of powder were placed inside sterile wells on a 6-well plate. Subsequently, different dices of poultry comparable by weight and dimensions (approximately 2.5 gr, 1 cm×1 cm) were set on circular PLA supports (diameter 30 mm×3 mm in height) previously sterilised by UV irradiation and placed inside the wells of the aforesaid plate. A well containing only the powder and the support was used as negative control, while a well containing only the poultry and the support was used as positive control. The plate was sealed with parafilm and incubated at 4° C. for 8 days. Subsequently, both the poultry and the support were removed sterilely; the liquids released by the meat and the powder present in the wells were recovered utilising 200 uL Luria-Bertani (LB) liquid medium and plated on different plates of LB agar and incubated O.N. at 37° C. The results were reported in the form of total direct bacterial count of a surface equal to 25% of the plate and subsequently normalising with respect to the total surface of the plate.

All tested powders demonstrated the capacity to strongly reduce the bacterial charge present in the liquids that are normally released by the meats of the study and that represent the water constituting the meat during the preservation period; i.e. the liquid obtainable from the "drip loss" phenomenon or losses of liquid by dripping during processing and preservation. The experiments were conducted in the absence of contact between the samples of meat and the powder, which was deposited below PLA circular supports on which the meat dice rested, so as to gelify in contact with the drip liquids.

After 8 days of incubation at 4° C., the images of the groups of samples were acquired by means of the microscope with a contrast 2.5× lens.

FIG. 7A shows a representative image of each group, respectively untreated meat (CTRL+), powder (2d1) (CTRL−), meat+powder (2d1) 200:1 weight/weight (A), meat+powder (2d1) 300:1 weight/weight (B), meat+powder (2d1) 400:1 weight/weight (C), and meat+powder (2d1) 500:1 weight/weight (D).

From the images of FIG. 7A it is possible to note that the untreated meat (CTRL+) has a high and diffused bacterial charge unlike the powder (2d1) (CTRL−) which does not have a significant bacterial charge and of the meat+powder (2d1) 200:1 weight/weight (A), meat+powder (2d1) 300:1 weight/weight (B), weight+powder (2d1) 400:1 weight/weight (C), and meat+powder (2d1) 500:1 weight/weight (D) which have a bacterial charge lower than the CTRL+ and proportional to the quantity of powder (2d1, INVENTION) used in the evaluation tests.

The bar chart of FIG. 7B shows the microbial charge, expressed as CFU/mL of each group, respectively untreated meat (CTRL+), powder (2d1) (CTRL−), meat+powder (2d1) 200:1 weight/weight (A), meat+powder (2d1) 300:1 weight/weight (B), meat+powder (2d1) 400:1 weight/weight (C), and meat+powder (2d1) 500:1 weight/weight (D).

Each figure is representative of three different experiments and is expressed as mean±standard deviation. The statistical comparisons were evaluated by t-test. The values of $P<0.01$ () and $P<0.005$ (*) were considered to indicate a statistically significant difference.

The studies conducted allow to show that in the meat preserved for 8 days in standard conditions (4° C., 75% humidity) a ratio between the weight of the meat and the powder (2d1) between 200:1 reduces the microbial charge in the drip liquid by 94% with respect to the positive control (CTRL+), constituted by the drip liquid of only the meat untreated with the powder of the invention; if the ratio between the weight of the meat and the powder (2d1) is 300:1, the bacterial charge is reduced by 75%.

Data superposable to those set forth above were obtained with beef.

In conclusion, as described in the example 5, the composition of the invention has shorter gelification times than the gelification times of the alginate/pectin composition described by De Cicco et al, (2014), International Journal of Pharmaceutics 473: 30-37 and a high capacity of absorbing the exudate. Moreover, as described in the example 5, the gel formed in situ when the composition of the invention is placed in contact with a wound has an improved adhesive capacity with respect to the adhesive capacity of the gel described in De Cicco et al, (2014), International Journal of Pharmaceutics 473: 30-37.

As described in the example 7, the gel formed by the composition of the invention also has a water vapour transmission rate that is adequate to maintain a balanced hydration of the wound.

As shown in the example 8, the specific composition of the invention improves cell migration in a statistically significant way with respect to the alginate/pectin composition, therefore its use in powder form is an important aid to the wound healing process.

As shown in the example 9, the specific composition of the invention can advantageously encapsulate an antimicrobial agent; moreover, the rate of release of the antimicrobial agent can advantageously be controlled because of the different weight ratio of the polysaccharides that constitute the particles of the powder.

As shown in the example 10, the specific composition of the invention is able to control the microbial development even without adding active ingredients having antimicrobial activity. Therefore the composition can usefully be employed in the field of food, in particular in the sector of food preservation. Fresh food, for example meats, fruit, vegetables, etc., release fluids that increase the possibility of microbial pollution and reduce the shelf-life of foods. The in situ gelifying powder being an adsorbent of liquids and humidity allows a prolongation of the quality, safety and sensorial properties of the food to be preserved, serving as active packaging for fresh food products.

Lastly, as described in the example 2, an additional advantage of the composition of the invention is that it allows to carry out the atomization process in milder conditions both in the case of nanospray drying, and in the case of minispray drying.

Further advantages of the composition in powder form of the invention are represented by having adequate flowability so that the powder can be diffused on the wound, and capacity to form a barrier gel that completely fills the cavity of the wound, minimising the bacterial charge and the formation of exudate; having capacity of reducing pain and blood loss when cleaning the wound because it maintains the gel properties over time even if the wound does not produce exudate; having low or no systemic toxicity; being biodegradable.

All the features listed above demonstrate that the specific composition in powder form object of the invention is able to improve the treatment of cutaneous wounds, especially of chronic and/or ulcerous wounds and it represents an improvement with respect to the prior art.

The invention claimed is:

1. A composition in powder form comprising the following polysaccharides

15%-60% by weight of alginic acid or sodium alginate,
15%-60% by weight of pectin,
5%-20% or 35%-70% by weight chitosan,
with respect to the total weight of the polysaccharides, and
wherein the % by weight of the polysaccharides is at least 90% with respect to the total weight of the powder.

2. A composition according to claim 1, wherein
the alginic acid or the sodium alginate has a mannuronic acid residue content greater than or equal to 55%, by weight with respect to the total weight of the alginic acid or of the sodium alginate, respectively;
and/or
the pectin has a degree of amidation (DA) greater than or equal to 2%;
and/or
the pectin has a degree of methoxylation (DM) lower than or equal to 48%
and/or
the chitosan has a molecular weight lower than or equal to 400000 Da.

3. A composition according to claim 1 comprising
at least one further polysaccharide and/or
at least one ingredient selected from: soothing agents, cicatrizing agents, growth factors, peptides, anti-inflammatory agents and antimicrobials and/or
at least one inorganic salt selected from: sodium carbonate and sodium or potassium bicarbonate.

4. A composition according to claim 1 comprising:
25%-60% by weight of sodium alginate,
25%-60% by weight of pectin,
5%-15% or 45-50% by weight of chitosan
with respect to the total weight of the polysaccharides.

5. Composition in powder form according to claim 1
comprising at least 95%, at least 97%, at least 99.9%, or constituted by 100% of polysaccharides with respect to the total weight of the powder
and/or
having particle diameter between 100 nm and 5 microns.

6. A method for treating a cutaneous wound in a patient, said method comprising applying to said wound the composition in powder form as defined in claim 1 in an effective quantity for treating said wound.

7. A method for preserving a food, said method comprising contacting fluid released by said food with the composition in powder form as defined in claim 1 in an effective quantity for preserving the food.

8. A composition according to claim 1 comprising:
46% by weight of sodium alginate
46% by weight of pectin,
7% by weight of chitosan
with respect to the total weight of the polysaccharides.

9. A composition according to claim 1 comprising:
26% by weight of sodium alginate
26% by weight of pectin,
47% by weight of chitosan
with respect to the total weight of the polysaccharides.

10. A composition according to claim 1 comprising:
15% by weight of sodium alginate
15% by weight of pectin,
70% by weight of chitosan
with respect to the total weight of the polysaccharides.

* * * * *